US005922690A

United States Patent [19]
Van Gorp et al.

[11] Patent Number: 5,922,690
[45] Date of Patent: Jul. 13, 1999

[54] DERMATAN DISULFATE, AN INHIBITOR OF THROMBIN GENERATION AND ACTIVATION

[76] Inventors: Cornelius L. Van Gorp, 8439 Point O'Woods, Springboro, Ohio 45066; Stephanie J. Brister; Michael R. Buchanan, both of 151 Kent Street, Hamilton, Ontario, Canada, L8P 3Z2; Robert J. Linhardt, 1422 Plum St., Iowa City, Iowa 52440

[21] Appl. No.: 08/795,099

[22] Filed: Feb. 6, 1997

Related U.S. Application Data

[60] Provisional application No. 60/016,218, Apr. 25, 1996.
[51] Int. Cl.$^6$ .................................................. A61K 31/715
[52] U.S. Cl. ................................ 514/54; 536/53; 536/54; 536/55.1
[58] Field of Search ............................... 514/54; 536/53, 536/54, 55.1

[56] References Cited

U.S. PATENT DOCUMENTS

| | | | |
|---|---|---|---|
| 3,207,664 | 9/1965 | Nomine et al. | 514/67 |
| 3,634,123 | 1/1972 | Eriksson et al. | 428/447 |
| 4,440,926 | 4/1984 | Mardiguian | 536/21 |
| 4,727,063 | 2/1988 | Naggi et al. | 514/56 |
| 4,745,106 | 5/1988 | Griffin et al. | 514/56 |
| 5,013,724 | 5/1991 | Petitou et al. | 514/54 |
| 5,547,994 | 8/1996 | Mascellini et al. | 514/54 |

FOREIGN PATENT DOCUMENTS

| | | |
|---|---|---|
| 2000650 | 10/1989 | Canada . |
| 554898 | 8/1993 | European Pat. Off. . |
| 2584728 | 1/1987 | France . |
| 3124384 | 1/1983 | Germany . |

OTHER PUBLICATIONS

Fernandez et al, "Catalysis of Thrombin Inhibition Provides an Inde for Esimating the Antithrombotic Potential of Glycosaminoglycans in Rabbis," *Thromb. Haemostas.*, (1987), pp. 286–293.

Fernandez et al, "The Hemorrhagic and Antithrombotic Effects of Dermatan Sulfate," *Brit. J. Haematol.*, 64 (1986), pp. 309–317.

Linhardt et al, "Dermatan Sulfate as Potential Therapeutic Agent," *Gen. Pharmar.*, 26, No. 3 (1995), pp. 443–451.

Ofosu et al, "Heparan Sulfate and Dermatan Sulfate Inhibit the Generation of Thrombin Activity in Plasma by Complementary Pathways," *Blood*, 64, No. 3 (Sep. 1984), pp. 742–747.

Okwusidi et al, "In Vivo Catalysis of Thrombin Inhibition by Antithrombin III or Heparin Co–Factor II and Antithrombotic Effect: Differential Effects of Unfractionated Heparin and Dermatan Sulfate," *Thromb. Haeorrh. Disorders*, 1, (1990), pp. 77–80.

Ryan et al, "Antithrombotic Properties of Dermatan Sulfate (MF701) in Haemodialysis for Chronic Renal Failure," *Thromb. Haemostas.*, 68 (1992), pp. 563–569.

Tollefsen et al, "The Interaction of Glycosaminoglycans with Heparin Cofactor II: Structure and Activity of a High–Affinity Dermatan Sulfate Hexasaccharide," *Plenum Press*, (1992), pp. 167–176.

Van Ryn–McKenna, "Dermatan Sulfate: A New Concept in Antithrombotic Therapy," *Diss. Abstr. Int.*, B 53, (1993), p. 5662.

Volpi et al, "Physico–Chemical Properties and the Structure of Dermatan Sulfate Fractions Purified from Plasma after Oral Administration in Healthy Human Volunteers," *Thromb. Haemostas.*, 75 (1996), pp. 491–496.

Whinna et al, "Interaction of Heparin Cofactor II with Biglycan and Decorin," *J. Biol. Chem.*, 268, (Feb. 1993), pp. 3920–3924.

Agnelli, "New Antithrombins and Nonheparin Glycosaminoglycans in Clinical Development," *Vessels*, 1 (1995), pp. 9–16.

Bergonzini et al, "Pharmacokineics of Native and Low Molecular Weight Dermatans: Preliminary Studies in Rats and Primates," *Seminars in Thrombosis and Hemostasis, Sup 2*, (1991), pp. 235–239.

Cifonelli et al, "," Unknown Journal, 233 (1958), pp. 541–545.

Brister et al, "Is Heparin the Ideal Anticoagulant for Cardiopulmonary Bypass? Dermatan Sulphate May Be an Alternate Choice,," *Thromb. Haemostas.*, 71 (1994), pp. 468–473.

Dietrich et al, "The influence of Preoperative Anticoagulation on Heparin Response During Cardiopulmnary Bypass," *J. Thorac. Cardiovasc. Surg.*, 102 (1991), pp. 505–514.

Dunstone et al, "Ion–Exchange Reactions Between Acid Mucopolysaccharides and Various Cations," *Biochem.J.*, 85, No. 3 (1962), pp. 336–351.

Edens et al, "Heparin and Derivatized Heparin Inhibit Zymosan and Cobra Venom Factor Activation of Complement in Serum," *Immunopharmoacol.*, 27 (1994), pp. 145–153.

Edens et al, "Heparin Is Not Just An Anticoagulant Anymore: Six and One–Half Decades of Studies on the Ability of Heparin to Regulate Complement Activity," *Complement Profiles*, (1993), pp. 96–120.

Fareed et al, "Molecular and Functional Heterogeneity in Dermatan Sulfate Preparations," *Seminars in Thrombosis and Hemostasis*, 17, supp 2 (1991), pp. 174–180.

(List continued on next page.)

*Primary Examiner*—Kathleen K. Fonda
*Attorney, Agent, or Firm*—Mark F. Smith; Eric W. Guttag; Smith, Knochelmann, Freese & Guttag

[57] ABSTRACT

A method of inhibiting thrombin generation and of inhibiting complement activation by using a dermatan sulfate having at least 2 sulfate groups per disaccharide obtained by chemical sulfation of native dermatan sulfate. The resulting dermatan sulfate having an average molecular weight from about 5000 to 35000 Daltons is characterized by (i) a high content of L-iduronic->4,6-di-O-sulfated N-acetyl-D-galactosamine residues, and (ii) a specific heparin cofactor II-mediated anti-thrombin activity, depending on average molecular weight, between about 25 to 125 U/mg.

46 Claims, 7 Drawing Sheets

OTHER PUBLICATIONS

Ferrari et al, "Preliminary Chemical, Biochemical, and Pharmacological Characterization of a Low Molecular Weight Dermatan Sulphate," *Carbohydrate Res.*, 255, No. 3 (1994), pp. 125–132.

Hemker et al, "Mode of Action of Heparin and Related Drugs," *Seminars In Thrombosis and Hemostasis*, 17, supp 1 (1991), pp. 29–34.

Hogg et al, "Fibrin Monomer Protects Thrombin from Inactivation by Heparinantithrombin III: Implications for Heparin Therapy," *Proc. Natl. Acad. Sci.*, 86 (May 1989), pp. 3619–3638.

Ireland et al, "Heparin as an Anticoagulant During Extracorporal Circulation," *Heparin*, (1989), pp. 549–574.

Kawai et al, "Chondroitin Polysulfate of Squid Cartilage," *Biochem*, 60 (1966), pp. 317–321.

Kiss, "β–Eliminative Degradation of Carbohydrates Containing Uronic Acid Residues," *Adv. Carbohydr. Chem. Biochem.*, 29 (1974), pp. 229–303.

Levy et al, "Chemical and Pharmacologica Studies on N–Resulfated Heparin," *Proc. Soc. Exp. Biol. Med..,* 109 (1962), pp. 901–905.

Linhardt et al, "Low Molecular Weight Dermatan Sulfate as an Antithrombotic Agent," *Biochem. Pharm.*, 47, No. 7 (1994), pp. 1241–1252.

Linhardt et al, "Analysis of Glycosaminoglycans with Polysaccharide Lyases," *Current Protocols in Molecular Biology*, (1995), pp. 2:17.13.17–17.13.32.

Maaroufi et al, "Influence of the Oversulfation Method and the Degree of Sulfation on the Anticoagulant Properties of Dermatan Sulfate Derivatives," *Thromb. Res.*, 59, (1990), pp. 749–758.

Maimone et al, "Structure of a Dermatan Sulfate Hexasaccharide that Binds to Heparin Cofactor II with High Affinity," *J. Biol. Chem.*, 265, (Oct. 1990), pp. 1863–1871.

Mascellani et al, "Quantitation of Dermatan Sulfate Active Site for Heparin Cofactor II by $^1$H Nuclear Magnetic Resonance Spectroscopy," *Anal. Biochem..,* 223 (1994), pp. 135–141.

Mascellani et al, "Relative Influence of Different Disulphate Disaccharide Clusters on the HCII–Mediated Inhibition of Thrombin by Dermatan Sulfates of Different Origins," *Thromb. Res.*, 74, (1994), pp. 605–615.

Matthiasson et al, "The Haemorrhagic Effect of Low Molecular Weight Heparins, Dermatan Sulphate and Hirudin," *Haemostasis*, 25 (1995), pp. 203–211.

Ogamo et al, "Reactivity Toward Chemical Sulfation of Hydroxyl Groups of Heparin," Carboh. Res., 193, (1989), pp. 165–172.

Seikagaku Kogyo Co., *Products for Life Science*, (1989).

Tollefsen et al, Heparin Cofactor II. Purification and Properties of a Heparin–Dependent Inhibitor of Thrombin in Human Plasma, *J. Biol. Chem.*, 257, (Mar. 1982), pp. 2162–2169.

Thomas et al, "Relative Efficacy of Heparin and Related Glycosaminoglycans as Antithrombotic Drugs," *Ann. N.Y. Acad. Sci.*, 556 (1989), pp. 313–322.

Uchiyama et al, "Changes in the Structure and Biological Property of N→O Sulfate Transferred N–Reulfated Heparin" *J. Biol. Chem.*, 4, (Apr. 1991), pp. 6756–6760.

Volpi et al, "Dermatan Sulfate from Beef Mucosa: Structure, Physicochemical and Biological Properties of Fractions Prepared by Chemical Depolymerization and Anion–Exchange Chromatography," *Carbohydrate Res.*, 255, (1994), pp. 133–144.

Weiler et al, "Heparin and Modified Heparin Inhibit Complement Activation In Vivo," *J. Immunol.*, 148, (May 1992), pp. 3210–3215.

Murata et al. *Renal Physiol.* 1978, 1(1), 48–55.

Mascellani et al. *Thrombosis Research* Oct. 1996, 84(1), 21–32.

Pavão et al. *J. Biol. Chem.* Dec. 1995, 270(52), 31027–31036.

Ofosu et al. *Biochem. J.* Dec. 1987, 248, 889–896.

Linhardt et al. *Biochemical Pharmacology* Sep. 1991, 42(8), 1609–1619.

Nagasawa et al, "Chemical Sulfation of Preparations of Chrondroitin 4– and 6–Sulfate, and Dermatan Sulfate Preparation of Chondroitin Sulfate E–Like Materals From Chondroitin," *Carbohydrate Research*, 158, No. 1 (Dec. 1986), pp. 183–190, Amsterdam, Netherlands.

DERMATAN DISULFATE, AN INHIBITOR OF THROMBIN GENERATION AND ACTIVATION

CROSS-REFERENCE TO PRIOR APPLICATION

This application claims benefit of Provisional Patent Application Ser. No. 60/016,218, filed Apr. 25, 1996.

BACKGROUND OF THE INVENTION

1. Field of the Invention

In general, this invention relates to an antithrombin III-independent, heparin cofactor II (hereinafter HCII) mediated inhibition of thrombin generation, as well as the inhibition of the alternative, classical and terminal pathways of complement activation; specifically, this invention relates to a chemically-sulfated dermatan sulfate composed of mainly disulfated disaccharide dermatan chains which inhibit thrombin generation and complement activation.

2. State of the Art

Conditions or diseases characterized by excessive generation of thrombin, such as deep vein thrombosis (hereinafter DVT) or destructive vascular smooth muscle cell (hereinafter VSMC) proliferation can be life threatening and require effective treatment. These conditions frequently occur after the subject has been exposed to trauma, such as that caused by surgery or other wounds. The trauma results both in vascular damage and VSMC proliferation, causing vascular stenosis, restenosis and hyperplasia, as well as activation of blood coagulation. Vascular restenosis, hyperplasia and activation of blood coagulation can be life threatening when occurring after vascular graft surgery, heart transplantation, balloon or laser angioplasty, arterial traumatic injury, post-surgical repair of muscular arteries, long term in-dwelling of arterial catheters, invasive arterial diagnostic procedures, kidney, lung or liver transplants, or bypass surgery procedures.

DVT, for example, frequently occurs before one life threatening complication, pulmonary embolism (hereinafter PE). The majority of PEs, and particularly, the majority of fatal PEs, follow an asymptomatic DVT. Epidemiological data indicate the rate of DVT each year to be about 160 per 100,000 in the general population, with the rate of fatal PEs about 60 per 100,000. Thus, the medical profession strives to treat DVT and prevent its complications. Ideally, a satisfactory treatment of DVT will prevent PE, extension of the thrombus, venous gangrene and limb losses, symptomatic recurrence of thrombosis, severe post-thrombotic syndrome, and progressive swelling of the leg resulting in increased compartmental pressure leading to subsequent phlegmasia cerulea dolens.

As an example of the seriousness of the problem, patients undergoing some sorts of elective surgery are at high risk of developing postoperative venous thromboembolism. It is known that without preoperative prophylaxis a high incidence, perhaps as high as 50%, of DVT accompanies total hip replacement with a consequent high rate of PE. However, anticoagulants are efficacious for the prevention of morbidity and mortality in the treatment of DVT (European Consensus Report; 1992) since it is known that anticoagulants, in general, and heparin in particular, can reduce DVT and fatal PE in general surgical patients. Heparin, a glycosaminoglycan (hereinafter GAG) having potent anticoagulant properties, is a heterogeneous mixture of variably sulfated polysaccharide chains having a molecular weight between about 5,000 to about 30,000 Daltons composed of repeating units of D-glucosamine and either L-iduronic or D-glucuronic acid residues. Therefore, prudent procedure dictates that before surgical intervention the patient receives anticoagulant prophylaxis, usually heparin, which is typically continued for 7 to 10 days postoperatively.

Other life threatening complications occur after surgical intervention to repair vascular damage. One serious form of vascular damage, atherosclerosis, causes nearly 50% of all mortality in North America from a diverse array of illness including heart attack, stroke and gangrene of the extremities. Usually, an excessive, inflammatory-fibroproliferative response to various forms of endothelium and arterial wall insult causes the atherosclerotic lesions. Frequently, the treatment of choice to combat atherosclerosis is surgical intervention, resulting in the over 1.5 million bypass graft, endarterectomy, and percutaneous translumenal angioplasty (hereinafter PCTA) procedures performed annually in North America. Unfortunately, in many instances, although the immediate effects of the procedure are beneficial to the surgical patient, later post-procedure acceleration of the arteriosclerotic process greatly reduces the long-term effectiveness of the surgical intervention. Specifically, VSMC proliferation in the intima frequently leads to stenosis and occlusion of the lumen of the vessel. For example, the restenosis rate following PCTA is as high as 40% in the first three to six months after the procedure. In the case of the over 200,000 bypass grafts performed annually, between 40 to 60% fail within five years due to proliferative and occlusive changes involving VSMC proliferation. Moreover, VSMC proliferation accounts for more than 50% of heart transplant failures within five years. Accordingly, there is a need for compositions and methods to reduce the acceleration of arteriolsclerotic processes occurring after cardiovascular procedures.

Drugs or other treatments interfering with the growth-promoting activity causing VSMC proliferation would slow progression of the atherosclerotic process. Since it is known that thrombin exerts a potent VSMC growth promoting activity, and, under certain conditions may be present within the vessel wall, thrombin inhibitors are prime candidates to slow the atherosclerotic process. Among the compositions that interfere with the effect of thrombin are commercial heparins, (Castellot, J. J. *J. Cell Biol.* 102: 1979–84 (1986)) which inhibit thrombin both in vitro and in vivo. Heparin is also thought to be a potent anti-proliferative inhibiting thrombin better than any of the other known GAG in vitro. (Castellot, J. J., et al. *J. Cell Biol.* 90: 3722 (1981)) However, there is little evidence to support the latter possibility in the clinical setting.

Moreover, heparin has many limitations caused primarily by its potent anticoagulant activity. For example, the high doses of heparin (>200 units/kg (hereinafter U/kg), which generates >3 antithrombin units/ml of plasma) required to perform successful cardiopulmonary bypass (hereinafter CPB) surgery and to maintain CPB pump patency causes local or profuse hemorrhage contributing to patient morbidity. Excessive post-operative blood loss and the consequent requirement for blood transfusion are well-documented adverse affects suffered by patients who undergo CPB surgery. (Woodman, R. D., Harker, L. A., Bleeding Complications Associated with Cardiopulmonary Bypass, *Blood* 76(9): 1680 (1990); Dietrich, W., et al., The Influence of Preoperative Anticoagulation on Heparin Response During Cardiopulmonary Bypass, *J. Thorac. Cardiovasc. Surg.* 102: 505 (1991)) Life threatening bleeding is reported in between 5 to 25% of cases and it is estimated that surgeons must reopen approximately three percent of CPB patients because of surgical bleeding. The bleeding complications are due, not only to surgical bleeds, but also to a displacement of heparin from various plasma proteins which results in prolonged systemic anticoagulation and to an inhibitory effect of heparin on platelet function. Administering a precise amount of heparin antagonist in the form of protamine reverses the anticoagulant effect of heparin and prevents excessive blood loss at the time of decannulation. However, protamine administration is critically dosage sensitive, and even modest excess protamine administration causes numerous alarming and potentially fatal side-effects, including platelet inhibition, prolongation of the activated partial thromboplastin time (hereinafter APTT), and prolongation of systemic hypotension and pulmonary hypertension. (Ireland, H., Rylance, P. B., Kesteven, P., Heparin as an Anticoagulant During Extracorporeal Circulation, *Heparin*, David A. Lane and Ulf Lindahl (Eds).; 549–74 (1989)) A 1985 survey of perfusionists cited "the protamine reaction" as the most frequent perfusion accident in CPB procedures, observed fully in two-thirds of the cases. (Kuruz, *6th Annual Meeting of Pathophysiology and Extracorporeal Technology*, San Diego, Calif. (1986)) Therefore, CPB provides an excellent in vivo model to evaluate the contribution candidate compounds or methods have on the exacerbation or the amelioration of antithrombotic activity and bleeding complications.

Heparin has also been used to treat complement system abnormalities. The complement system, plays a major role in host defense both through destruction of invading organisms and through mediation of inflammation. Complement abnormalities are unusual conditions characterized by a deficiency or by a dysfunction of any of the more than nineteen normally well-behaved proteins constituting about 10% of the globulins in normal human serum. Patients with complement deficiencies or with complementary dysfunctions also may be susceptible to tissue injury as a result of excessive inflammatory responses. Further, complement activation in the course of recovery from temporary blood vessel occlusion or in response to cardiopulmonary bypass during heart surgery initiates tissue damage beyond that caused by the initial injury. Heparin has been shown to inhibit activity of the alternative, classical and terminal pathways of complement by regulating C1, C1 Inhibitor, C4 binding protein, C3b, factor H and S-protein in a model that predicts in vivo complement inhibition properties. (Edens, R. E., Linhardt, R. J., Bell, C. S., Weiler, J. M., Heparin and Derivatized Heparin Inhibit Zymosan and Cobra Venom Factor Activation of Complement in Serum, *Immunopharmacol*. 27: 145153 (1994)) However, the anticoagulant activity of heparin contributes to an increased risk of bleeding, electrolyte shifts and thrombocytopenia.

In an effort to counteract thrombus formation and bleeding caused by the systemic administration of heparin during CPB surgery, methods for site-specific administration of heparin have been developed involving coating antithrombotic compounds on blood-interacting biomaterials. The antithrombotic compound may be bound either ionically or covalently onto a biomaterial polymer surface. A major disadvantage with polymers coated with currently available heparin formulations is the limited efficacy of heparin. Therefore, it is important to develop new coating compositions which optimize antithrombotic activity while being applied satisfactorily and consistently to a variety of materials such as natural polymers and synthetic plastics. Such new compositions will, ideally, result in complete coverage of the blood-interacting surfaces of a medical article.

Heparin is a natural product, and, as is the case with many products obtained from different biological sources, heparin can vary in its structure, particularly in the degree of sulfation. Selective O-sulfation enhances the activity of some heparins and heparin-like GAGs. Whale heparin, for example, having a low degree of O-sulfation, can be selectively 6-O-sulfated as the tributylammonium salt in dimethylformamide (Uchiyama, H., Metori, A., Ogamo, A., Nagasawa, K. J. *Biochem*. 107: 377 (1990); Ogamo, A., Metori, A., Uchiyama, H., Hagasawa, K. *Carboh. Res*. 193: 165–172 (1989)) to increase its anticoagulant activity. Pyridium salts of heparan sulfate, another GAG with a low level of N- and O-sulfation, have been sulfated (Ofosu, F. A., Modi, G. J., Blachman, M. A., Buchanan, M. R., Johnson, E. A. *Biochem. J*. 248: 889 (1987)) to increase biological activity. Alternatively, GAGs, being soluble in water or formamide (Kiss, J. *Helv. Chimica. Acta*. 50: 1423 (1967); Griffin, C. C., Stevenson, J. R., Foley, K. M. *XIVth Int. Carbohydr. Symp., Stockholm* (1988)), have also been sulfated by treatment with pyridine or trialkyl amines sulfur trioxides complexes, the latter being preferred because of its stability. (Levy, L., Petacek, F. J. *Proc. Soc. Exp. Biol. Med*.109: 901 (1962)) Increasing the degree of sulfation improves the catalytic effects of dermatan sulfate (hereinafter DS) on the inhibition of thrombin by HCII in plasma. (Ofosu, F. A., Modi, G. J., Smith, L. M., Cerskus, A. L., Hirsch, J., Blajchman, M. A. *Blood* 64: 742–47 (1984)) Other studies have suggested a potential as antithrombotic drugs for slightly over-sulfated derivatives of dermatan sulfate. (Maaroufi, R. M., Tapon Bretaddiere, J., Mardiguian, J., Sternberg, C., Dautzenberg, M. D., Fischer, A. M., Influence of the Oversulfation Method and the Degree of Sulfation on the Anticoagulant Properties of Dermatan Sulfate Derivatives. *Thromb. Res*. 59: 749–758 (1990)) However, none of these over-sulfated GAGs have been shown to overcome the difficulties noted above for heparin in the clinical setting.

Recent studies provide other rationales for replacing heparin as a thrombin inhibitor. For example, thrombin may bind to fibrin in vitro. This binding significantly impairs the ability of heparin to catalyze thrombin inhibition (Hogg, D. J., Jackson, C. M., Fibrin Monomer Protects Thrombin from Inactivation by Heparin antithrombin III: Implications for Heparin Therapy, *Proc. Natl. Acad. Sci*. 86: 3619–238 (1989)) because heparin must bind both to the high affinity site on ATIII, and to the thrombin anionic exosite—the same site at which thrombin binds fibrin—to catalyze thrombin inhibition. Therefore, thrombin bound to fibrin impairs the access of the exosite to heparin/ATIII, greatly reducing the effect of heparin as a thrombin inhibitor.

Use of heparin allows complex vascular surgical procedures. However, as can be seen from the above discussion, heparin, particularly if administered systemically, is not the ideal candidate drug for inhibition of thrombosis, the prevention of accelerated arteriosclerosis involving VSMC growth, or inhibition of complement activation that accompanies vascular procedures and organ transplants.

One promising replacement candidate for heparin is dermatan sulfate, a heparin-like GAG, also known as β-heparin or chondroitin sulfate B. Dermatan sulfate is a polysaccharide composed of repeating uronic acid->N-acetyl-D-galactosamine disaccharides joined by alternating 1,3 and 1,4 linkages. Depending on its source and the method of preparation, it can have a molecular weight as high as 50,000 Daltons. Initially, it is formed as a polymer composed of repeating uronosyl->N-acetyl-D-galactosamine disaccharide units attached to the core protein via a glucuronosyl->galactosyl->galactosyl->xylosyl linkage region. Since the monomeric components of dermatan sulfate are saccharides, they are susceptible to epimerization. In particular, in the biosynthesis of dermatan sulfate, some of the D-glucuronic acid residues are epimerized at C-5, converting them to L-iduronic acid residues, followed by O-sulfation of N-acetyl-D-galactosamine primarily at C-4, but also at C-6. Dermatan sulfate typically has sulfur and nitrogen contents between about 6.2 to 6.9% and between about 2.4 to 2.9%, respectively (Seikagaku America, Inc. 3 (1989)), which structurally reflects a dermatan monosulfated disaccharide, referred to herein as dermatan sulfate (DS).

It has been shown that dermatan sulfate and chondroitin sulfate components in cartilage are solely responsible for the cation-binding capacity, that the cation-binding reactions are of the ion-exchange type and that different cations exhibit varying degrees of affinity for the cartilage. (Dunstone JR, Ion-Exchange Reactions Between Acid Mucopolysaccharides and Various Cations. *Biochem J.* 85: 336–351 (1962))

In animal models, DS has been demonstrated to be a potent antithrombotic agent with low risk of hemorrhage. (Fernandez, F., Van Rijn, J., Ofosu F. A., Buchanan, M. R., The Hemorrhagic and Anthrombotic Effects of Dermatan Sulfate, *Brit. J. Haematol.* 64: 3 (1986)) A 500 μg/kg dose of DS inhibits thrombus formation as well as a 70 μg/kg dose of heparin. At higher doses, the amount of bleeding from a standardized incision in a rabbit's ear was much greater with heparin than with DS, indicating that DS is more efficient and safer as an anticoagulant than heparin, suggesting that DS would be useful clinically to inhibit thrombus formation without triggering massive hemorrhage. In addition, DS has little in vitro effect on platelets, and one may inject up to forty times the antithrombotic dose of DS in rabbits without increasing bleeding. (Fernandez, F., Van Rijn, J. Ofosu, F. A., Hirsch, J., Buchanan, M. R., The hemorrhagic and antithrombotic effect of dermatan sulfate. *Br. J. Haematol.* 64: 309–1 (1986)) Moreover, DS has been shown to effectively catalyze the inhibition of thrombin in vitro, regardless of whether it is fibrin-bound or free, (Okwusidi, J. I., Anvari, N., Kulczycky, M., Blajchman, M. A., Buchanan, M. R., Ofosu, F. A., In vivo Catalysis of Thrombin Inhibition by Antithrombin III or Heparin Co-factor II and Antithrombotic Effect: Differential Effects of Unfractionated Heparin and Dermatan Sulfate, *Thomb. Haemorrh. Disorders.* 1: 77–8013 (1990)), and to inhibit both thrombin and fibrin accretion onto preformed rabbit thrombi more effectively than heparin in vivo. DS (30 U/kg) has also been shown to inhibit hyperplasia of 1st and 2nd injury carotid arteries in a rabbit model in which heparin (150 U/kg) had no effect. (Buchanan M. R., Brister S. J. Inhibition of Injured Vessel Wall Restenosis with Acute Thrombin Inhibition. Relative Effects Of Heparin and Dermatan Sulfate. *Bk of Abst. Joint Conf Arteriosclerosis, Thrombosis, Vascular Biol*, Salt Lake City, Utah. p. 18 (Feb. 18–20, 1987)).

DS specifically activates HCII, a plasma protease inhibitor, which inhibits thrombin but not other proteases involved in hemostasis. (Tollefsen, D. W., Majerus, D. W., Blank, M. K., Heparin Cofactor II. Purification and Properties of a Heparin—Dependent Inhibitor of Thrombin in Human Plasma, *J. Biol. Chem.* 257:2162–9 (1982)) HCII is activated by DS fractions of 12 or more residues in length that contain an octasaccharide sequence required for binding to the inhibitor. A hexasaccharide component in DS with high affinity to HCII has been identified. (Tollefsen, D. M., In: Lane, D. A., Bjurk, I., Lindahl, U (Eds.), Heparin and Related Polysaccharides. *Plenum Press*, New York, pp. 167–7 (1992)).

DS inhibits thrombin through an ATIII-independent pathway by accelerating HCII-dependent inhibition of thrombin.

(Ofosu, F. A., Modi, G. J., Blachman, M. A., Buchanan, M. R., Johnson, E. A. *Biochem. J.* 248: 889 (1987)) DS contains some amount of oversulfated sequences (IdoA2S-GalNAc4S) and (IdoA-GalNAc4S6S) besides the major monosulfated disaccharide sequence (IdoA-GalNAc4S). The concentration of the oversulfated sequences in naturally occurring DS correlates with the HCII-mediated inhibition of thrombin. (Mascellani, G., Liverani, L., Prete, A., Guppola, P. A., Bergonzini, G., Bianchini, P., Relative Influence of Different Disulphate Disaccharide Clusters on the HCII-mediated Inhibition of Thrombin by Dermatan Sulfates of Different Origins, *Thromb. Res.* 74: 605–1517 (1994)) It has been suggested that the L-iduronic acid content in DS correlates with increased thrombin inhibition. (Whinna H. C., Choi H. U., Rosenberg L. C., Church F. C. Interaction of Heparin Cofactor II with Biglycan and Decorin, *J. Biol Chem.* 268: 3920–3924 (1993) DS has less specific anticoagulant activity than heparin, as demonstrated by comparing their activities. Compared to heparin 150 U/mg, DS has an activity of less than 5 U/mg, as measured by the APTT. (Thomas, D. P., Merton, R. E., Barrowcliffe, T. W., Relative Efficacy of Heparin and Related GAGs as Antithrombotic Drugs, *Ann. N.Y. Acad. Sci.* 556: 313–22 (1989)) DS has been demonstrated to be an effective anticoagulant for DVT prophylaxis in patients undergoing elective orthopedic surgery, for preventing thrombus formation in patients undergoing hemodialysis, and for performing successful cardiopulmonary bypass in adult pigs experimentally. (Van Rijn, J., McKenna, J., Dermatan Sulfate: A New Concept in Antithrombotic Therapy, *Diss. Abstr. Int.* B 53: 5662 (1993)); (Ryan, K. E., Lane, D. A., Flynn, A., Ireland, H., Boisclair, M., Sheppard. J., Curtis, J. R., Antithrombotic Properties of Dermatan Sulfate (MF701) in Haemodialysis for Chronic Renal Failure. *Thom Haemostas* 68: 563 (1992); (Brister S. J., Ofosu, F. A., Heigenhauser G. L. F., Gianese, F., Buchanan M. R., Is Heparin the Ideal Anticoagulant for Cardiopulmonary Bypass? Dermatan Sulphate May Be ab Alternate Choice. *Thom Haemostas* 71: 468–73 (1994)).

Unfortunately, however effective DS is in the laboratory, it causes practical clinical problems because of its low specific biological activity combined with high viscosity and poor solubility. Therefore, administering DS is cumbersome and impractical.

It has now been discovered that the biological activity of DS typically having one sulfate group per disaccharide may be significantly increased by the addition of another sulfate group. It also has been found that the resulting composition, dermatan disulfate (hereinafter DDS) consisting principally of repeating disulfated disaccharide residues not only is an effective thrombin inhibitor in vivo, but also effectively inhibits complement activation; and attenuates vessel wall hyperplasia. This is especially true for DDS consisting primarily of L-iduronic acid->4,6-di-O-sulfated-N-acetyl-D-galactosamine units (IdoA-GalNAc4S6S). Furthermore, it was found, that DDS inhibits thrombin generation more effectively than heparin during CPB.

As has been noted, DS comprises primarily monosulfated monomers, although some monomers in naturally occurring DS will be over-sulfated. Those DS polymers having a high L-iduronic acid content have been correlated with increased thrombin inhibition. (Whinna, H. C., Choi, H. U., Rosenberg, L. C., Church, F. C., Interaction of Heparin Cofactor II with Biglycan and Decorin, *J. Biol. Chem.* 268: 392S3924 (1993)) Moreover, it has been further suggested that increasing the degree of sulfation of DS improves the catalytic effects of inhibition of thrombin by HCII in plasma. (Ofosu, F. A., Modi, G. J., Smith, L. M., Cerskus, A. L., Hirsch, J., Blajchman, M. A. *Blood* 64: 742–47 (1984)) Other studies on slightly oversulfated derivatives of DS have suggested their potential as antithrombotic drugs. (Maaroufi, R. M., Tapon Bretaddiere, J., Mardiguian, J., Sternberg, C., Dautzenberg, M. D., Fischer, A. M,. Influence of the Oversulfation Method and the Degree of Sulfation on the Anticoagulant Properties of Dermatan Sulfate Derivatives, *Thromb. Res*. 59: 749–758 (1990)).

A linear correlation has been found in the content of disulfated disaccharide residues and the HCII mediated activity for dermatan sulfate fractions containing up to 20% of 2,4-O-disulfated disaccharides (IdoA2S-GalNAc4S). However, when the content of 2,4-O-disulfated disaccharides residues was low, even considerable concentrations of 4,6-O-disulfated disaccharides residues (IdoA-GalNAc4S6S) failed to contribute to antithrombin activity. (Mascellani, G., Liverani, L., Prete, A., Bergonzini, G., Bianchini, P., Torri, G., Bisio, A., Guerrini, M, and Casu, B., Quantitation of Dermatan. Sulfate Active Site for Heparin Cofactor II by H-Nuclear Magnetic Resonance Spectroscopy, *Anal. Biochem*. 223: 135–141 (1994)) Other studies attribute a high HCII-mediated inhibition of thrombin generation principally to dermatan sulfate fractions containing about 3% of 4,6-O-disulfated disaccharide sequences. (Linhardt, R. J., Desai, U. R., Liu, J., Pervin, A., Hoppensteadt, D., Fareed, J., Low Molecular Weight Dermatan Sulfate as an antithrombin agent, *Biochem. Phanncol*. 47: 1241–1252 (1994)) More recently, it was suggested that 4-O-sulfation of the N-acetyl-D-galactosamine residues is essential for the anticoagulant activity of DS and that the structure which binds to HCII is repeating 4-O-sulfated-L-iduronic->4-O-sulfated-D-galactosamine sequences. (Pavao, M. S. G., Mourao, P. A. S., Mulloy, B., Tollefsen, D. M., *J. Biol. Chem*. 270: 31027–36 (1995)).

Bovine mucosa and pig skin are a primary source for commercial dermatan sulfates preparations containing 2,4-O-disulfated disaccharide residues. (Mascellani, G., Liverani, L., Prete, A., Bergonzini, G., Bianchini, P., Torri, G., Bisio, A., Guerrini, M, and Casu, B., Quantitation of Dermatan. Sulfate Active Site for Heparin Cofactor II by H-Nuclear Magnetic Resonance Spectroscopy, *Anal. Biochem*. 223: 135–141 (1994)) Porcine mucosa derived dermatan sulfates typically have 4,6-O-disulfated disaccharide residues as well. (Mascellani, G., Liverani, L., Prete, A., Bergonzini, G., Bianchini, P., Torri, G., Bisio, A., Guerrini, M, and Casu, B. *Anal. Biochem*. 223: 135–141 (1994); Linhardt, R. J., Desai, U. R., Liu, J., Pervin, A., Hoppensteadt, D., Fareed, J., Low Molecular Weight Dermatan Sulfate as an antithrombin agent, *Biochem. Phanncol*. 47: 1241–1252 (1994)) A GAG from squid cartilage, also known as Chondroitin Sulfate E, is composed principally of 4,6-O-disulfated disaccharides. However, it is composed principally of D-glucuronic->4,6-O-disulfated-N-acetyl-D-galactosamine units (Kawai, Y., Seno, N., Anno, K., J. Biochem. 60: 317 (1966)) rather than L-iduronic->4,6-O-disulfated-N-acetyl-D-galactosamine (IdoA-GalNAc4S6S).

The degree of sulfation is an important functional property that contributes significantly to the anticoagulant effect of DS and other heparin-like GAGs. In DS, the galactosamine unit is typically O-sulfated and O-sulfate groups are often present at the 4-position and occasionally at the 6-position. The 2- and/or 3-position of iduronic acid are occasionally sulfated, as well.

SUMMARY OF THE INVENTION

It has now been found that dermatan sulfate (DS) typically having one sulfate group per disaccharide is at least as effective an anticoagulant as heparin, prevents thrombin generation more effectively than heparin, and attenuates intimal hyperplasia more effectively than heparin. We found that these biological activities may be significantly improved with the addition of an additional sulfate group. It has also been found that the resulting dermatan disulfate (DDS) consisting principally of repeating L-iduronic acid->4,6-O-disulfated disaccharide residues not only is an effective thrombin inhibitor, but also effectively inhibits complement activation.

One aspect of this invention is a method of inhibiting thrombin generation by administering a composition containing an effective amount of dermatan disulfate (DDS) composed of repeating L-iduronic acid->N-acetyl-D-galactosamine disaccharide having more than 2 sulfate groups per disaccharide.

Another aspect of this invention is a composition containing an effective amount of dermatan disulfate (DDS) composed of more than about 75% repeating L-iduronic acid->4,6-O-disulfated-N-acetyl-D-galactosamine disaccharide units, and a molecular weight between about 5000 and about 30,000 Daltons.

Another aspect of this invention is a formulation containing an effective amount of dermatan disulfate (DDS) composed of repeating L-iduronic acid->N-acetyl-D-galactosamine disaccharide units having more than 2 sulfate groups per disaccharide.

DETAILED DESCRIPTION OF THE PREFERRED EMBODIMENT

Dermatan sulfate (DS), refers to a preparation obtained from tissues in a manner conventional for the preparation of DS, otherwise synthesized, or obtained commercially. DS is characterized by having little or no ATIII related activity and having HCII related anticoagulant activity in vitro. Biosynthesis epimerizes some of the D-glucuronic acid residues at C-5 converting them to L-iduronic acid residues. Then N-acetyl-D-galactosamine is O-sulfated primarily at C-4 and secondarily at C-6. Those skilled in the art understand the sequence of steps involved in the biosynthetic epimerization and sulfation well. Mammalian tissues, for example, mammalian skin, including, if desired, human tissue serve as sources for DS. Generally, vascularized tissue and skin from porcine or bovine sources are preferred as sources for DS, intestinal mucosa providing the preferred commercial source of DS. In general, the DS starting material is prepared from the selected tissue source by allowing the tissue to undergo hydrolysis and collecting the polyanions by anion exchange chromatography followed by selective precipitation of DS with copper sulfate.

Figure 1:
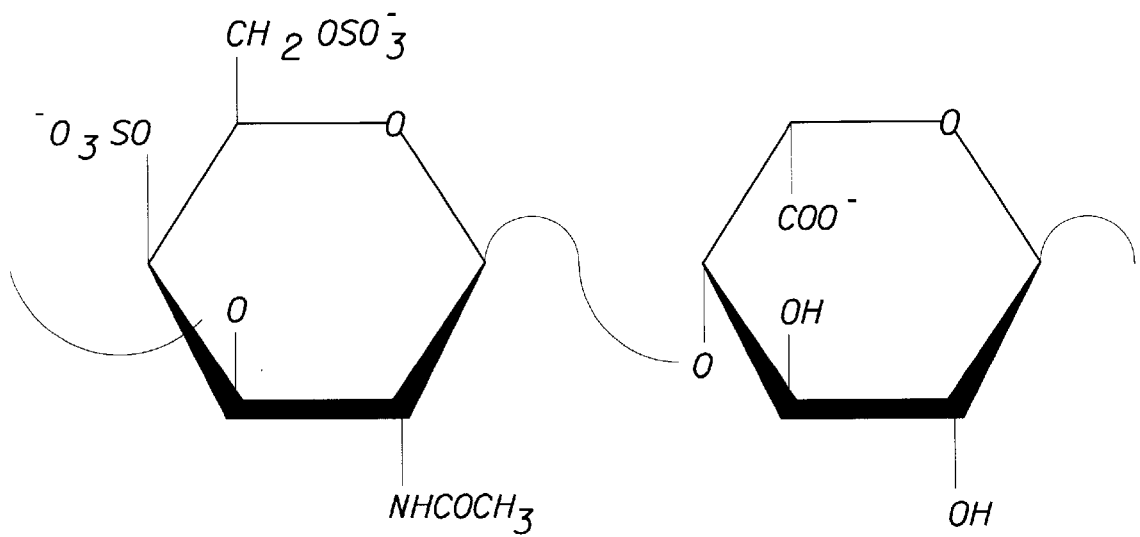
FIG. 1 shows a diagram of the chemical composition of a typical disaccharide in the DDS composition of the invention.

Referring now to FIG. 1, a dermatan disulfate (DDS) of the present invention is shown comprising a mixture of dermatan polymeric chains principally containing connected disulfated disaccharide dimers obtained by chemical sulfation of native DS. Preferably, the polymers of this invention comprise repeating L-iduronic acid->N-acetyl-D-galactosamine disaccharide units having more than 2 sulfate groups per disaccharide. It is also preferred that the polymers of this invention comprise repeating L-iduronic acid->N-acetyl-D-galactosamine-4,6-O-disulfated disaccharide units. Preferably, the polymers of this invention have an average molecular weight ranging between about 5,500 to about 37,500 Daltons, preferably between about 5,000 to about 30,000 Daltons, corresponding to about 16 to about 100 monosaccharide units in the polymeric chains.

The DDS having an average molecular weight less than about 30,000 Daltons is preferably obtained by cleaving longer chain polysaccharides either (1) by sulfation of a fragment of the native dermatan sulfate (DS), or (2) by depolymerization of the DDS.

Dermatan chains are depolymerized by a variety of enzymatic and chemical methods known to those skilled in the art, including those in which (1) chondroitinase cleaves native dermatan sulfate linkages between N-acetyl galactosamine and uronic acid with the formation of oligosaccharides bearing 4,5-unsaturated uronic acid residues at the non-reducing end (Linhardt, R. J., In: Current Protocols in Molecular Biology. A Varki, ed. 2:17.13.17–17.13.32 (1995); (2) esters of the iduronic carboxyl groups of dermatan are subjected to β-elimination (Kiss, J., Adv Varbohydr Chem. Biochem, 29: 229–303 (1974)) at alkaline pH (Mardiguian, J. S., U.S. Pat. No. 4,440,926 (1984)) with the formation of 4,5-unsaturated uronic acid at the non-reducing end; (3) nonsulfated uronic acid residues of dermatans are cleaved by oxidation with periodate, followed by reduction of the resulting dialdehydes with borohydride and hydrolysis under mild acidic conditions (Wolfrom, M. L., Wang, P. Y., Honda, S., Carbohydr Res. 11:179 (1969)), thus producing end groups with the remnant of the nonsulfated uronic acid; (4) the glycosidic bonds of dermatans are cleaved by a radical mechanism using hydrogen peroxide, known as oxidative-reductive depolymerization (Gilbert, D. L., Gershman, R., Ruhm, K. B., Price, W. E., *J. Gen Physiol*, 41:989 (1958)); (Pigman, W., Hawkins, W., Grauling, E., Rizi, S., Holley, H., Arch Biochem Biophys, 89:184 (1960)); (Pigman, W., Rizvi, S., Biochem Biophys Res Comm 1:39 (1959)), resulting in fragments having reducing end groups, and (5) dermatan chains are cleaved concomitant with sulfation by the action of a mixture of sulfuric and chlorosulfonic acids. (Naggi, A., Torri, G., U.S. Pat. No. 4,727,063 (1988)) The polymers of this invention have significant ATIII-independent antithrombin activity mediated through the action of HCII.

Generally, DDS is preferably synthesized by sulfating native dermatan sulfate (DS). Commercially obtained DS dissolved in a polar solvent, preferably, a polar solvent such as water or formamide or an aprotic polar solvent such as dimethylformamide, is treated with a sulfating agent, preferably a mild sulfating agent such as tri-lower-alkylamine-sulfur trioxide complex, where lower-alkyl is hereinafter defined to include alkyl radicals of five or fewer carbon atoms, at a temperature between about −20° to 100° C. for between about one hour to forty eight hours. Any iduronic acid residues not containing either or both a 2-sulfate or 3-sulfate and galactosamine residues not containing a 4-sulfate or a 6-sulfate would therefore be susceptible to sulfation; however, the susceptible galactosamine residues are sulfated much more rapidly than the iduronic acid residues, giving the reaction a great degree of selectivity. This degree of selectivity allows especially active anticoagulant formulations of DDS to be prepared. The prepared DDS can form a salt. Preferred cations for salt formation are selected from the group comprising barium, calcium, copper, lithium, sodium, potassium, zinc, and ammonium ions selected from the group consisting of $NR_1R_2R_3R_4^+$ where the R groups can be the same or different lower alkyl groups or hydrogen. It is preferred that the reaction mixture be purified by charge density fractionation. DDS can also be derivatized to introduce reactive groups to permit its binding onto blood-interacting devices by reductive amination. In one embodiment, it is preferred that DDS be complexed to an amine, preferably an amine that allows radiation grafting onto blood-interacting biomaterials.

DDS can be made to "stick" to biomaterials by electrostatic means. Quaternary ammonium salts can bind to adsorptive surfaces and may therefore be used to coat biomaterials that come in contact with blood. The positive amine radicals of primary, secondary and tertiary amines and quaternary ammonium compounds electrostatically bind the negative sulfate radicals of DDS. Quaternary ammonium salts selected from the group consisting of $NR_1R_2R_3R_4^+$ where between one and four of the R groups can be the same or different aryl groups, alkyl groups, providing that at least one group is an alkyl having more than 8 carbon atoms, or hydrogen. Quaternary ammonium salts, such as benzalkonium chloride, an alkyl-dimethylbenzyl-ammonium chloride in which the alkyl group ranges from C8 to C18 are preferred for this function. Alkyl radicals having between 16 and 18 carbon atoms have similar binding properties regardless of what other radicals are bound to the amine group. Reduction of the number of carbons on the alkyl groups to 12 results in a significant decrease in the degree of surfactant-plastic surface fixation. DDSs complexed with quaternary ammonium salts physically bind onto adsorptive surfaces because of their potent surface-active properties and may thus be used to coat artificial materials which contact the blood stream. Copolymers of amines and DDS also may be irreversibly attached to polymers by gamma irradiation, a technique of radiation grafting known in the art.

In one preferred synthesis, a reaction mixture is dissolved in formamide containing commercially available DS in a concentration between about 2.5% to 25% (wt/volume), but preferably about 7.5% (w/v), and incubated with the trimethylamine-sulfur trioxide complex for more than 4, preferably more than 6, hours. While the reaction proceeds well at between about 10° C. and 30° C., preferably about room temperature, lower temperature may be preferred to enhance reaction selectivity. The preferred range of temperatures may be in the range of between about −10° C. and 60° C. The resulting composition contains modified disulfated (and trisulfated) disaccharides of molecular weights in the range of between about 5000 to 35000 Daltons with an average chain length of between about 16 to 100 monosaccharide units, having at least 75% of the residues having more than 2 sulfate groups per disaccharide, and an in vitro HCII mediated antithrombin activity, depending on average molecular weight, of about 25 to 125 U/mg. In a typical preparation the HCII-mediated antithrombin activity of the commercially available DS preparation used for the synthesis (usually about <10 U/mg) is increased more than 2-fold, preferably more than 8 fold to between about 25 to 125 U/mg, depending on molecular weight. The inhibition of thrombin generation and complement activation by the preparation is greater than that of the original native DS on a gravimetric basis.

The composition so synthesized, DDS, is useful as a general anticoagulant for blood, and so may be used in the collection and analysis of blood in vitro, as a coating on biomaterials that contact blood, or therapeutically where inhibition of thrombin generation and/or inhibition of complement activation is desirable. DDS preferably possesses an anti-IIa activity in the range of between about 25 to 125 U/mg, and more preferably greater than 75 U/mg.

The antithrombotic DDS compositions of the invention are useful in therapeutic applications for treatment of conditions or diseases that are characterized by excessive generation of thrombin and complement activation. These conditions frequently occur where the subject has been exposed to trauma, such as in the case of surgical patients. The trauma caused by wounds or surgery results not only in vascular damage and secondary smooth muscle cell proliferation which result in vascular restenosis and hyperplasia, but also in activation of blood coagulation. These undesirable results can occur after vascular graft surgery, heart transplantation, balloon or laser angioplasty, arterial traumatic injury, post-surgical repair of muscular arteries, long term in-dwelling of arterial catheters, invasive arterial diagnostic procedures, kidney, lung or liver transplants, and bypass surgery procedures. The efficacy of DDS for treating the above listed conditions can be tested by using pig and/or rabbit models.

For example, the effects of DS and heparin on hyperplasia were tested as follows: Rabbit carotid arteries were injured by fluid pressure dilation. Half of the animals were treated over 2 hours pre/post-injury with 30 U/kg of DS or with 150 U/kg of heparin. Four weeks later, the animals were killed and the degree of injured vessel wall hyperplasia was determined histologically, using a computer assisted image analyzer. The other half of animals were not treated at the time of 1st injury, but were allowed to recover. Two weeks later these animals were anesthetized and both injured carotid arteries (now occluded due to hyperplasia) were isolated. A carotid endarterectomy was performed on each occluded vessel to restore blood flow. At the time of the 2nd injury, each animal was treated with DS or heparin, as described above, and allowed to recover for another four weeks. These animals were killed and vessel wall hyperplasia was determined. DS attenuated vessel wall hyperplasia in both injury models. Heparin had no effect.

For all of these diseases and conditions, administration of suitable amounts of the compositions of the invention is useful. Preferred modes of administration include in vivo administration by parenteral administration, adventitial administration, intraluminal administration to the vascular wall, and implantation of the composition. It can also be used ex vivo. Administration is by typical routes and generally includes systemic administration, such as by injection. Particularly preferred is intravenous injection, as continuous injection over long time periods can be easily continued. Also preferred are introduction into the vascular system through intraluminal administration of by adventitial administration using osmotic pumps. Typical implants contain biodegradable materials such as collagen, polyactate, polylactate/polyglycoside mixtures, and the like, preferably formulated as patches or beads.

Typical dosage range from about 0.1–5 mg/kg/hr on a constant basis over a period of between about 5 to 30 days, preferably between about 7 to 14 days. The particularly preferred dosage is about 0.3 mg/kg/hr, or, in the case of a 70 kg adult, 21 mg/hr or about 300 mg/day.

For convenience, other, more conventional modes of administration, may be used as well. Injecting subcutaneously or intra-muscularly at a lower dose or administering orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the localization of the trauma is accessible. Formulations suitable for the foregoing modes of administration are known in the art, and a suitable compendium of other formulations is found in *Remington's Pharmaceutical Sciences*, Mack Publishing Company, Easton, Pa., latest edition.

The DDS compositions of the invention may also be bio-labeled using conventional methods including radiolabeling, fluorescent labeling, chromophores or enzymes. The DDS compositions can also be used in a competitive assay for antithrombotic amount in a biological sample. Antibodies specifically immunoreactive with DDS may be made by well known conventional procedures, and may be beneficially used as labels for the above tests.

EXAMPLES

The invention can be better understood by reference to the following illustrative Examples of the preferred embodiment of the invention. The Examples are meant to illustrate the invention and not to limit the scope of the invention in any way.

Example 1

This example shows the preparation of dermatan disulfate (DDS).

Under constant agitation, 67 grams of native dermatan sulfate (Celsus Laboratories, Cincinnati, Ohio, Lot No. DI-10494) having an average molecular weight of 36,000 Dalton, an optical rotation of −62°, a heparin assay of 5 u/mg and a HCII/anti-IIa activity of 7 U/mg was solubilized in 900 ml formamide previously dried over 4 Å molecular sieves. Then, 100 grams (32 mmol) of trimethylamine sulfur trioxide was added to the reactor which was protected from moisture with a calcium chloride drying tube. The mixture was reacted for 24 hours at 60° C. The product of the reaction was transferred to 1 liter of 95% ethanol, and held for 30 minutes before the addition of between 5 to 10 liters of 1% aqueous sodium chloride solution. The pH was adjusted to neutrality and the solution sanitized, decolored and diafiltered against 5 volumes of 1% aqueous sodium chloride (until all free trimethylamine had been removed from the reaction mixture) followed by 2 volumes of purified water. The product was concentrated and lyophilized, yielding 58 grams of DDS. TABLE 1 shows the properties of the DDS isolated from the reaction.

TABLE 1

Typical Properties of Dermatan Disulfate

| | |
|---|---|
| Average MW | 28,000 |
| Optical Rotation | -41.3° |
| Heparin Assay, u/mg | 10 |
| Nitrogen, % | 1.80 |
| Total Sulfur, % | 8.24 |
| Anti-IIa, U/mg | 88 |

Anti-IIa Activity—The HCII-mediated antithrombin activity of DDS was determined by incubating 80 μl of a sample solution containing 0.3 ml of sample (5.345 μg/ml) and 0.1 PEU of purified human Heparin Cofactor II (Sold by Celsus Laboratories, Cincinnati, Ohio, Catalog #44405), with 20 μl of purified human thrombin (7.5 NIH units/ml) at 37° C. for 180 seconds. Then, 50 μl of chromogenic substrate (2.5 μmol/ml of Ethyl Malonyl-Pro-Arg-pNA, sold by Celsus Laboratories, as Chromogenic THII, Cat.#01505) was added and the amidolytic thrombin activity measured at 405 nm. Measurements were performed on an ACL 300 Plus (Instrumentation Laboratory, Lexington Mass.) and calculated as compared to the USP Heparin Reference Standard K-3 (U.S. Pharmacopeial Convention, Inc., Rockville Md.).

Average Molecular Weight—The average molecular weight was determined by dissolving samples to 0.8% w/v in 0.5M sodium chloride. The outflow time in seconds was measured with an Ostwald capillary viscometer in a water bath equilibrated to 25° C. and the molecular weight calculated, as previously described.

Nitrogen and Sulfur—Nitrogen and sulfur contents were determined by elemental analysis (ASTM 5291 and D4239, respectively) by Galbraith Laboratories (Knoxville, Tenn.).

Figure 2A:
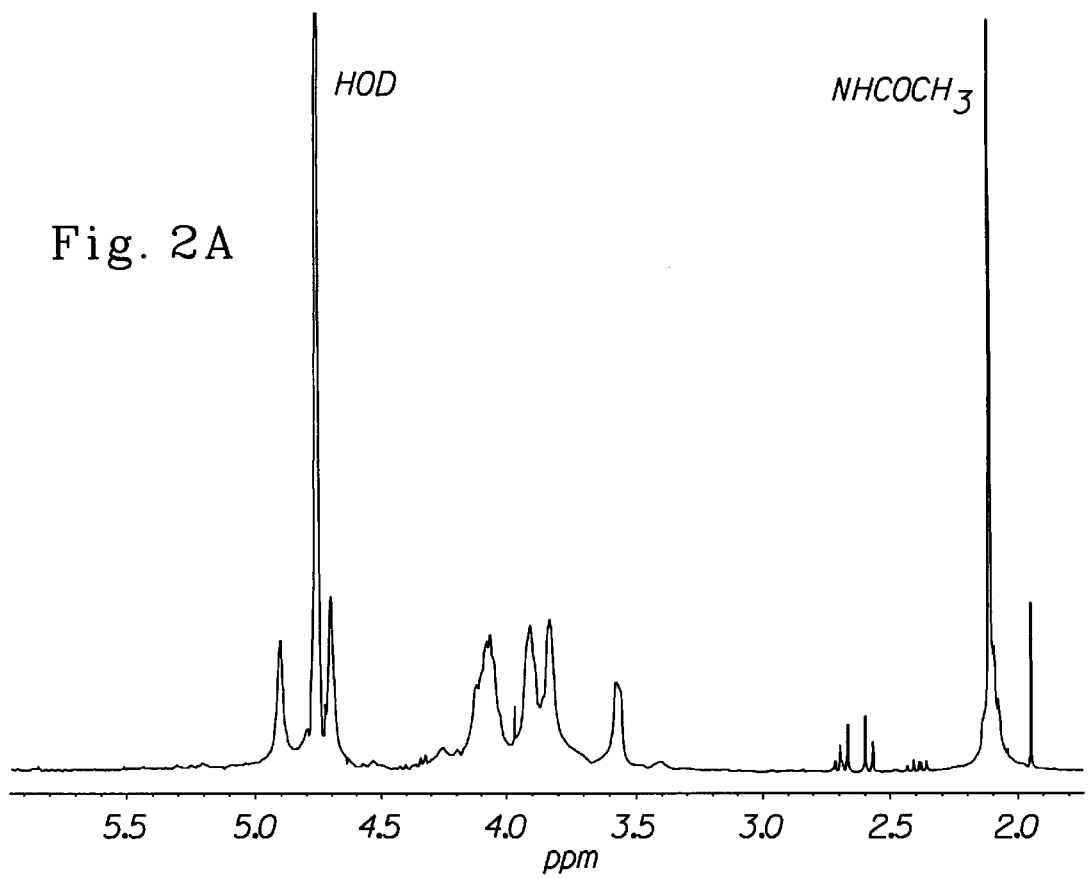
FIGS. 2a and 2b show, respectively, the H-NMR spectra at 500 mHz in D20 of the parent, native dermatan sulfate (DS) and the DDS-Composition of the Invention.
Figure 2B:
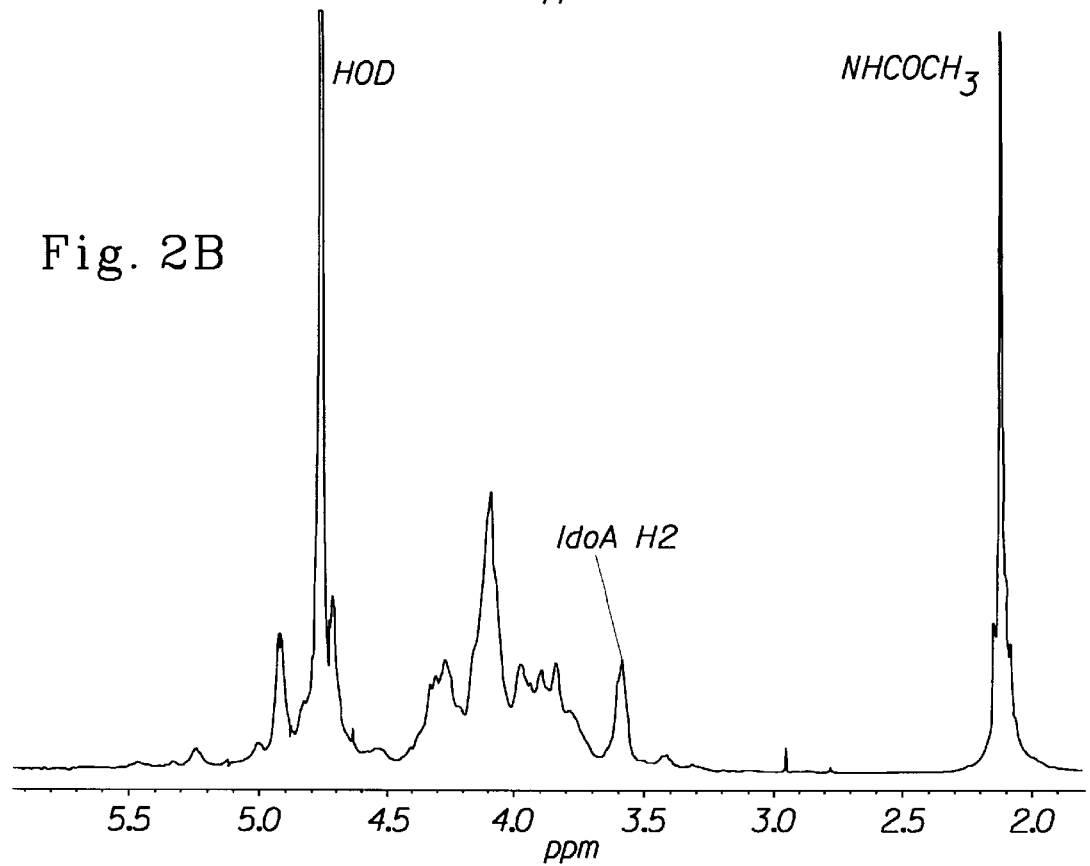
Figure 3A:
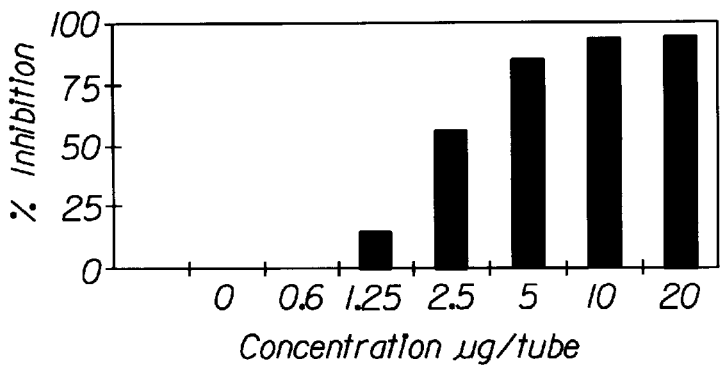
FIGS. 3a, 3b, and 3c, show, respectively, graphical representations of the percent compliment inhibition versus concentration by DDS, DS, (parent), DS (commercial), and heparin.
Figure 3B:
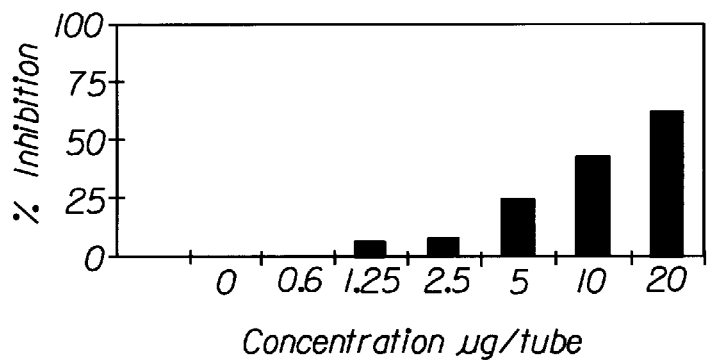
Figure 3C:
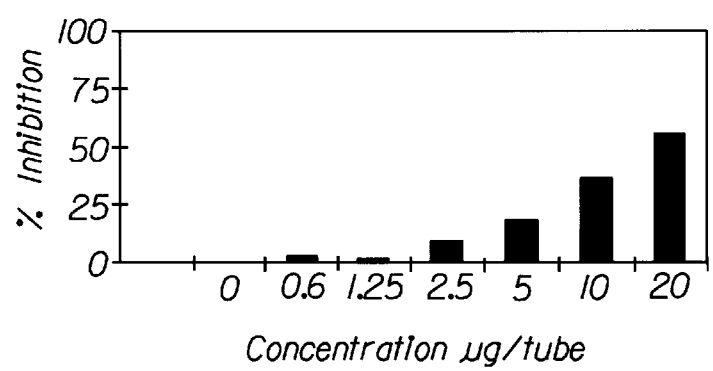
Figure 3D:
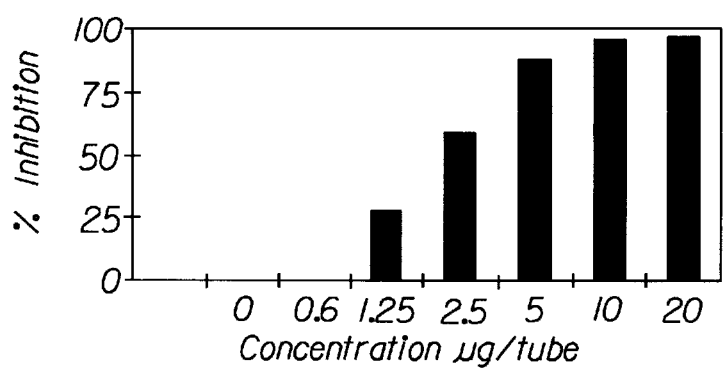

NMR Analysis—Samples of DS and DDS were exchanged with $D_2O$ (deuterium oxide) before an approximately 5% (w/v) dilution for H-NMR. The H-NMR spectra were recorded with 0.24 Hz digital resolution and at 60° C. to prevent the HOD signal from overlapping the broad signals from δ 4.64 to 4.74. The spectra of DS and DDS are shown in FIGS. 2a and 2b, respectively. Although generally similar, the two spectra differ at δ 4.1 representing an increased content of 4,6-O-disulfated-N-acetyl-D-galactosamine for DDS. FIG. 2a shows that DS is a typical native DS containing only iduronic acid residues and appears to be fully 4-O-sulfated. FIG. 2b shows that DDS is also completely 4-O-sulfated (δ 4.9), but is also almost entirely 6-O-sulfated (δ 4.1) containing a small amount of 2-O-sulfated iduronic acid (δ 5.25) and a trace of 2,3-di-O-sulfated iduronic acid (δ 5.48).

Example 2

This Example shows in vitro antithrombin III- and HCII-mediated inhibition of thrombin generation in the presence of DDS or heparin.

Blood was collected from a healthy human volunteer and dispensed into separate tubes each containing 25 anti-IIa U/ml of DDS or heparin. In vitro thrombin generation over time was approximately the same for both compounds. However, the majority of the anti-IIa activity of DDS was associated with HCII while the majority of the anti-IIa activity of heparin was associated with ATIII. See Table 2.

TABLE 2

| | Thrombin Generated in pMol | | | | |
|---|---|---|---|---|---|
| Time in Minutes | 15 | 30 | 60 | 120 | 240 |
| Heparin, T/HCII | 42 | 53 | 44 | 51 | 48 |
| Heparin, TAT | 24 | 25 | 26 | 28 | 41 |
| Heparin, Total | 66 | 78 | 70 | 79 | 89 |
| DDS, T/HCII | 56 | 42 | 48 | 54 | 61 |
| DDS, TAT | 15 | 07 | 09 | 12 | 07 |
| DDS, Total | 71 | 49 | 57 | 66 | 68 |

Example 3

This Example shows the in vitro complement inhibitory activity of DDS.

Heparin, DS and DDS were tested for their ability to regulate the classical pathway of complement as previously described and were prepared at various concentrations from 0.15 to 40 μg in 100 μl of half-isotonic veronal-buffered saline, pH 7.5, containing 0.1% gelatin, 0.15M calcium, 0.5 mM magnesium and 2.5% dextrose (DGVB++) and added to tubes on ice. Then, guinea pig C2 (C2gp), pre-titered to produce an average of one hemolytic event per cell (one Z of lysis) was added to each tube in 100 μl of DGVB++. Lastly $1 \times 10^7$ of sheep erythrocytes that contained surface C1 and C4 (EAC 1,4b) in 100 μl of DGVB++ were added to each tube and the tubes were immediately incubated in a shaking water bath at 30° C. for 10 minutes (the tmax). Then, 0.3 ml guinea pig concentrate (GPC) diluted in gelatin-veronal buffered saline that contained 40 mM ethylene-diamine was added to each tube as a source of terminal complement pathway components and incubation was continued for 60 minutes at 37° C. Finally, 1.5 ml of saline was added to each tube (except the 100% lysis tubes which received water), the tubes were shaken and centrifuged and lysis was assessed by determining hemoglobin release at 414 nm. Tubes that contained no GAG or GAG derivatives were designated as non-inhibited control and were constituted to have about one hemolytic event per cell (one Z of lysis). Reagent blank and 100% lysis tubes received neither GAGs nor C2. Inhibition was calculated based upon the lysis of cellular intermediates (Z) in the test sample compared with the non-inhibited control tubes.

Referring now to FIG. 3a through 3d a comparison of the complement inhibition activity of DDS (FIG. 3a), parent DS (FIG. 3b), commercial DS (FIG. 3c) and heparin (FIG. 3d) is shown. It can be seen that DDS of FIG. 3a has essentially the same inhibitory activity as the heparin of FIG. 3d, but considerable more activity than the DS of either FIG. 3b or 3c.

Example 4

This Example shows the use of DDS as compared to heparin and DS, in a CPB procedure in an adult pig.

Adult Yorkshire pigs (60–70 kg) were anesthetized with ketamine, intubated and ventilated (tidal volume 15 mg/kg, rate 12–16 per minute). Adequacy of ventilation was monitored continuously by measuring pH, pCO3 and pO2 levels in blood samples collected serially throughout the experiment. Anesthesia was maintained with Ethrane (Anaquest, Mississauga, Ontario) and intravenous Somnotol (MTC Pharmaceutical, Cambridge, Ontario). Paralysis, when necessary, was maintained with intravenous Pancuronium (Abbott STD, Abbott Laboratories, Saint Laurent, Quebec). Bilateral femoral arterial and venous lines were inserted to monitor blood pressure, to collect additional blood samples and to administer fluids and the test compound.

The CPB circuit consisted of polyethylene tubing and cannulae (Baxter Health Care, Bentley Division, Irvine Calif.), a membrane oxygenator with venous reservoir (Cobe CML, Cobe Canada Ltd., Scarborough, Canada) and an arterial in-line filter (Pall Stat Prime Blood filter, Pall Biomedical Inc., Figuerido, Puerto Rico). The circuit was primed with Ringer' lactate. Blood flow was regulated, using a Sarns roller pump (Model #5000, Sarns Inc. Ann Arbor, Mich.) and body temperature was regulated and monitored using a Sarns 3M HeaterCooler (Model #48103).

Pigs were anesthetized and prepared as described above. Their chests were opened via a median sternotomy. Then, the pigs were given either a bolus dose (400 U/kg) of heparin or DDS given as a bolus or as a bolus plus infusion. The compound was also added to the pump prime in a concentration equal to the expected plasma concentration to avoid any plasma dilution effect associated with the commencement of CPB. Next, aortic and atrial cannulae were secured in place and CPB was started.

Anticoagulant activities, arterial resistance, circuit occlusion, and blood loss were assessed as follows:

Anticoagulant Activities—Anticoagulant activity was measured as i) prolongation of activated clotting time (ACT) and ii) anti-thrombin and anti-factor Xa activities (U/ml) in blood samples collected immediately before injecting the compound and in blood samples collected serially during and up to 120 min post CPB. The ACT was measured in a Hemocron R-400 (International Technidyne Corp., New Jersey). The anti-thrombin and anti-factor Xa activities were measured, using standard chromogenic assays.

Blood Loss—All of the blood lost at the surgical site into the thoracic cavity before and after decannulation was collected, and its volume measured. All of the sponges which were used to pack the chest cavity post CPB were placed into 1 liter of water to lyse the red cells. The amount of blood was then determined by measuring the amount of hemoglobin present in the water spectrophotometrically. Total blood loss was calculated as the sum of these two measurements.

Assessment of Thrombus Fonnation—At the end of CPB and decannulation, the CPB circuit was drained of the blood and all components were inspected for visible thrombi and fibrin strands.

Thrombin/ATIII (TAT) Complexes—Thrombin is a key enzyme in the pathogenesis of thrombosis and is formed when prothrombinase cleaves prothrombin into thrombin and prothrombin fragments. Once formed in plasma, thrombin is inhibited by a naturally-occurring antiproteinase, ATIII, with formation of a complex of thrombin/ATIII (TAT). (Teitel, J. M., Bauer, K. A., Lau, H. K., Rosenberg, R. D., Studies of the prothrombin activation pathway utilizing radioimmunoassay for the F2/F1+2 fragment and thrombin-antithrombin complex, *Blood* 59: 1086–97 (1990)) It has been demonstrated that pre-operative TAT levels correlate with the risk of developing DVT after major surgery. For assays, blood was drawn into a vacutainer tube ((Becton Dickinson #6416); Becton Dickinson, Mountain View Calif.) containing 0.105 buffered citrate. Plasma was immediately separated from cellular elements by centrifugation at 1700×g for 15 minutes at 22° C., and frozen in aliquots at −70° C. until batch assays were performed. TAT levels were measured using a commercially available ELISA kit (Behringwerke, Marburg, Germany).

Thrombin/Heparin Cofactor II complexes (T/HCII)—Heparin Cofactor II (HCII) is a second endogenous inhibitor of thrombin in human plasma. DS/HCII dependent inhibition of thrombin suppresses thrombus formation, thrombus growth and hyperplasia in rabbits more effectively then heparin/ATII. Studies have suggested that HCII is a more effective inhibitor of thrombin which is compartmentalized in the extravascular space or bound to the surface of an injured vessel wall, formed thrombus or artificial surface (VanRyn-McKenna J., Ofosu F. A., Gary E., Hirsh J., Buchanan M. R. Effects of dermatan sulfate and heparin on inhibition of thrombus growth in vivo. *Ann NY Acad Sci*; 556: 304 (1989)); (Ofosu F. A., Fernandez F., Gauthier D., Buchanan M. R. Heparin Cofactor II and other endogenous factors in the mediation of the antithrombotic and anticoagulant effects of heparin and dermatan sulfate. *Semin Throm Haemost*; 11: 133 (1985)); (Okwusidi J. I., Anvari N., Kulczycky M., Blajchman M. A., Buchanan M. R. Fibrin moderates the catalytic action of heparin but not that of dermatan sulfate on thrombin inhibtion in human plasma. *J Lab Clin Med*; 117: 359 (1991)). For assays, the blood was processed for the TAT levels.

Figure 4:
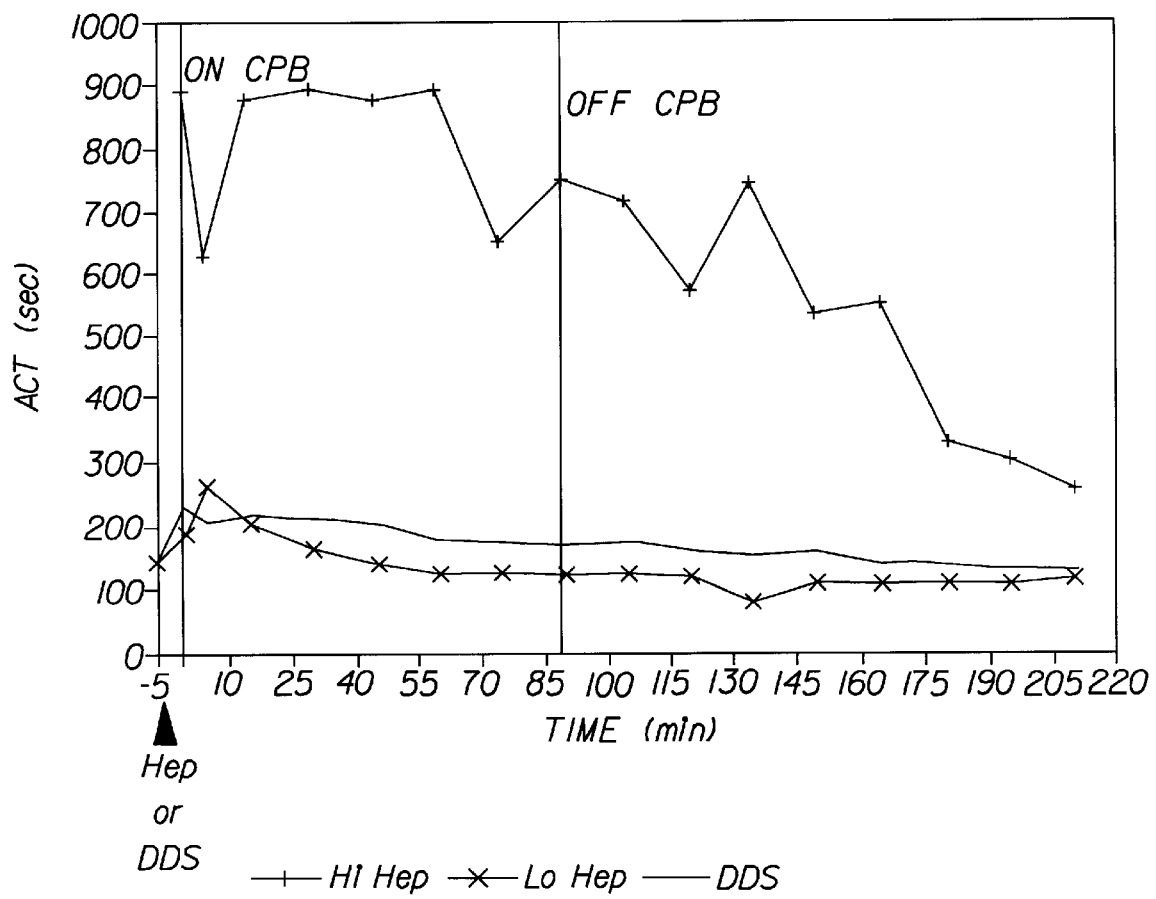
FIG. 4 shows a graphical representation of the activated clotting times (ACT) in pigs during and post CPB receiving 400 U/kg of heparin, 25 U/kg of heparin and DDS.
Figure 5:
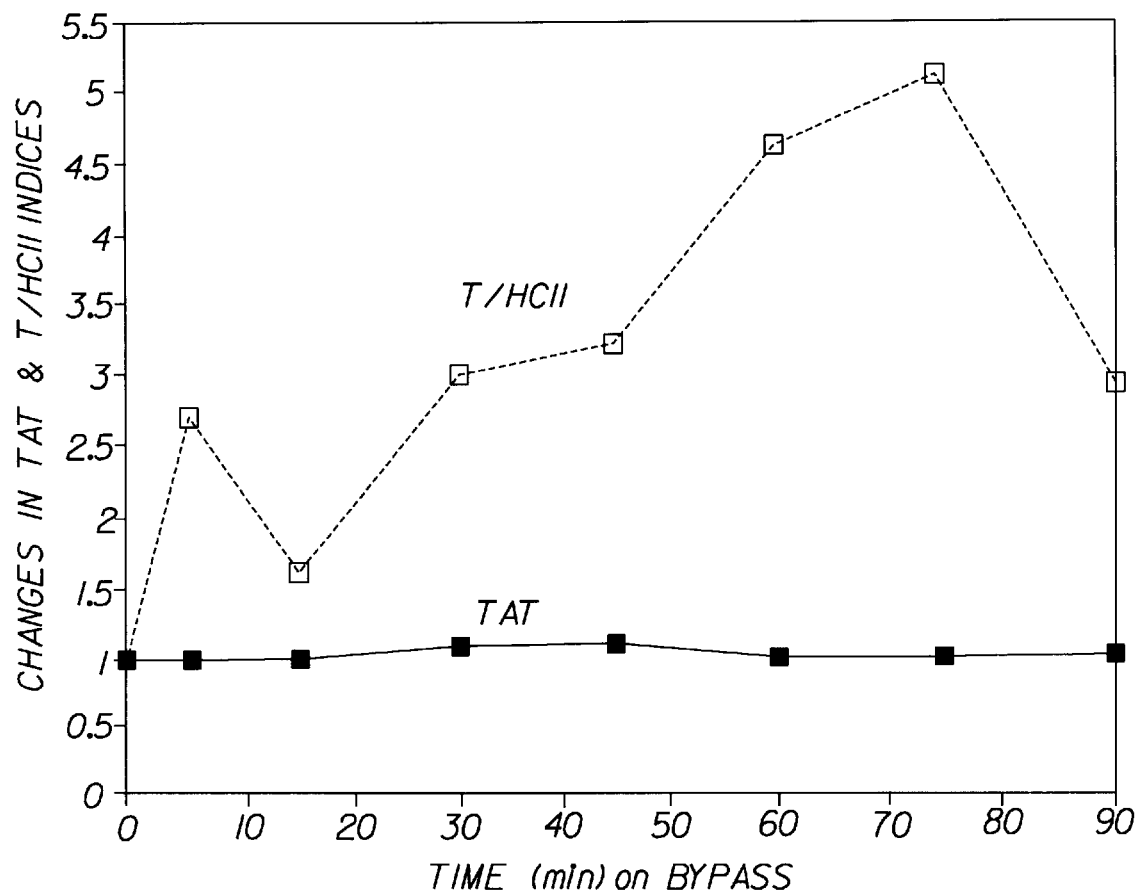
FIG. 5 shows a graphical representation changes in TAT and T/HCII levels versus time in a pig undergoing CPB with DDS anticoagulation.

Based on the specific (ATIII+HCII-mediated) anti-thrombin activity of 10 units, an 0.8 mg/kg bolus of DDS (lot #OD-00195, Celsus Laboratories, Cincinnati, Ohio) was administered to adult pigs (67–70 kg) followed by 2.4 mg/kg/hr infusions of DDS during CPB for ninety minutes, thus administering a total of 4.4 mg/kg of DDS (This compares to a typical dose of 2.67 mg/kg of heparin with an activity of 150 U/mg). CPB was successfully performed despite a modest prolongation of activated clotting time (ACT) to 270 seconds while on CPB. This ACT was associated with minimal anti-thrombin levels and nondetectable anti-Factor Xa levels. More importantly, the ACT returned rapidly to within the baseline measurements when the infusion was halted (See FIG. 4). The bulk of the thrombin generated during CPB was inhibited by HCII, as was demonstrated by the increased levels of thrombin/HCII (T/HCII) complexes in FIG. 5. This contrasts markedly with what is seen clinically and experimentally with heparin where the ACTs are prolonged greater than 700 seconds, and the TAT levels remain elevated for at least 24 hours, while both TAT and T/HCII levels rapidly returned to baseline upon discontinuation of DDS. This drop in TAT and T/HCII levels post-CPB suggests DDS/HCII inhibits thrombin more effectively than heparin/ATIII.

Comparative Example—A total of twelve animals, were placed on CPB and were administered 1 of 3 treatments prior to initiation of CPB.

---

Series 1 DDS 25
  n = 4  Dermatin disulfate 25 U/kg bolus, (2.5 mg/kg)
    (Celsus Laboratories, Cincinnati, Ohio, Lot No. OD-00195)
Series 2 HEP 25
  n = 4  Heparin 25 U/kg bolus (17 mg/kg) (Organon, Canada, Ltd., Toronto, Canada)
Series 3 HEP 400
  n = 4  Heparin 400 U/kg bolus (2.7 mg/kg) (Organon, Canada, Ltd., Toronto, Canada) (This is the standard dose used in CPB in humans.)

---

CPB was successful in both the high dose heparin-treated animals and in the DDS-treated animals; namely, there were no macroscopic clots seen in the circuits during CPB, the blood remained fluid post-CPB, and the animals suffered no untoward effects. This contrasts markedly with CPB in the low dose heparin treated animals in which clots were visible during CPB, the blood in the circuit clotted when the flows were reduced when coming off CPB, thereby making it impossible to go back on CPB if necessary. This need occurs approximately 30% of the time clinically. Moreover, the clotted blood is lost to the patient, thereby increasing the risk of post-operative bleeding and the use of homologues blood products. Blood loss was less in DD25 or HEP25 animals in comparison to HEP400 treated pigs. See Table 3.

TABLE 3

Chest Wall Bleeding, ml/2 hours

| Drug | No. of animals | Mean (+SEM) | P-value |
|---|---|---|---|
| HEP 400 | 6 | 161 ± 36 | |
| HEP 25 | 4 | 114 ± 21 | 0.594 |
| DDS 25 | 4 | 81 ± 13 | 0.07 |

Figure 6:
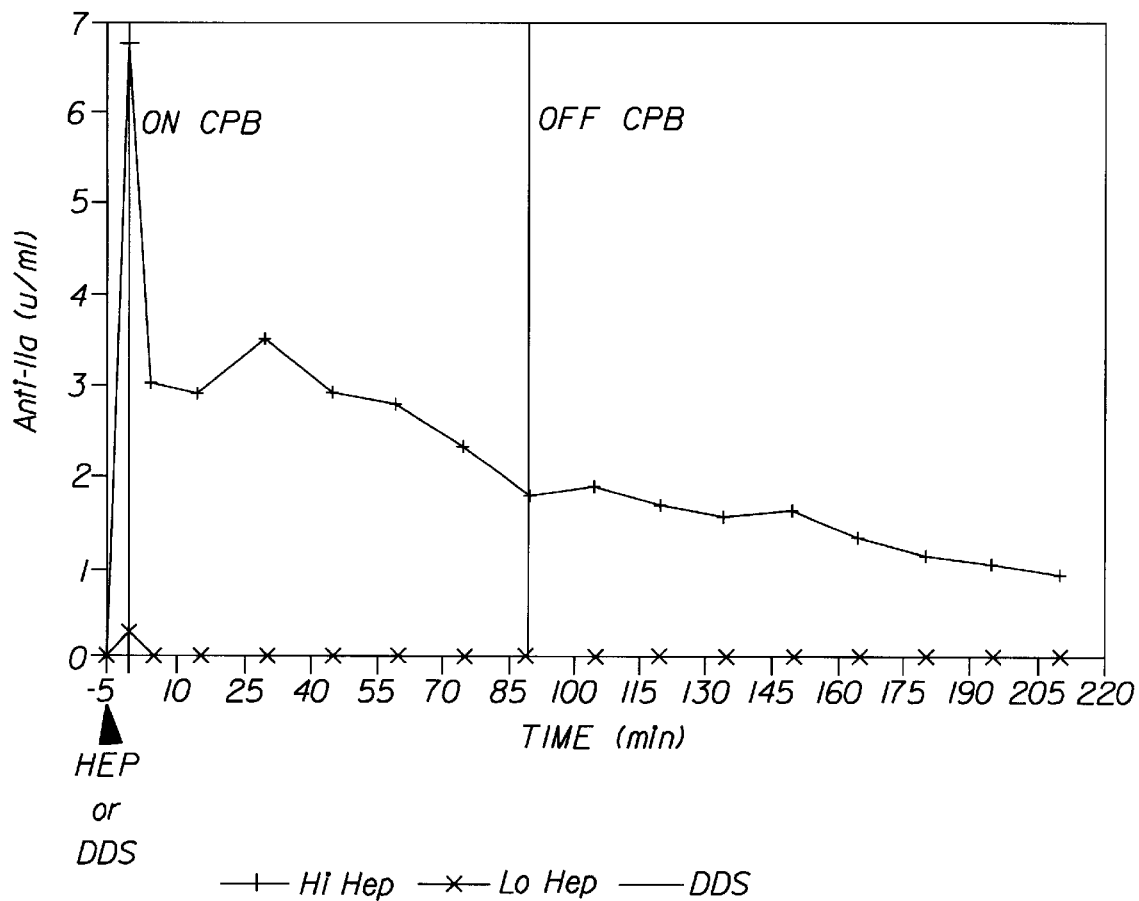
FIG. 6 shows a graphical representation of the Antithrombin activity versus time in a pig during and post CPB receiving 400 U/kg of heparin, 25 U/kg of heparin and DDS.
Figure 7:
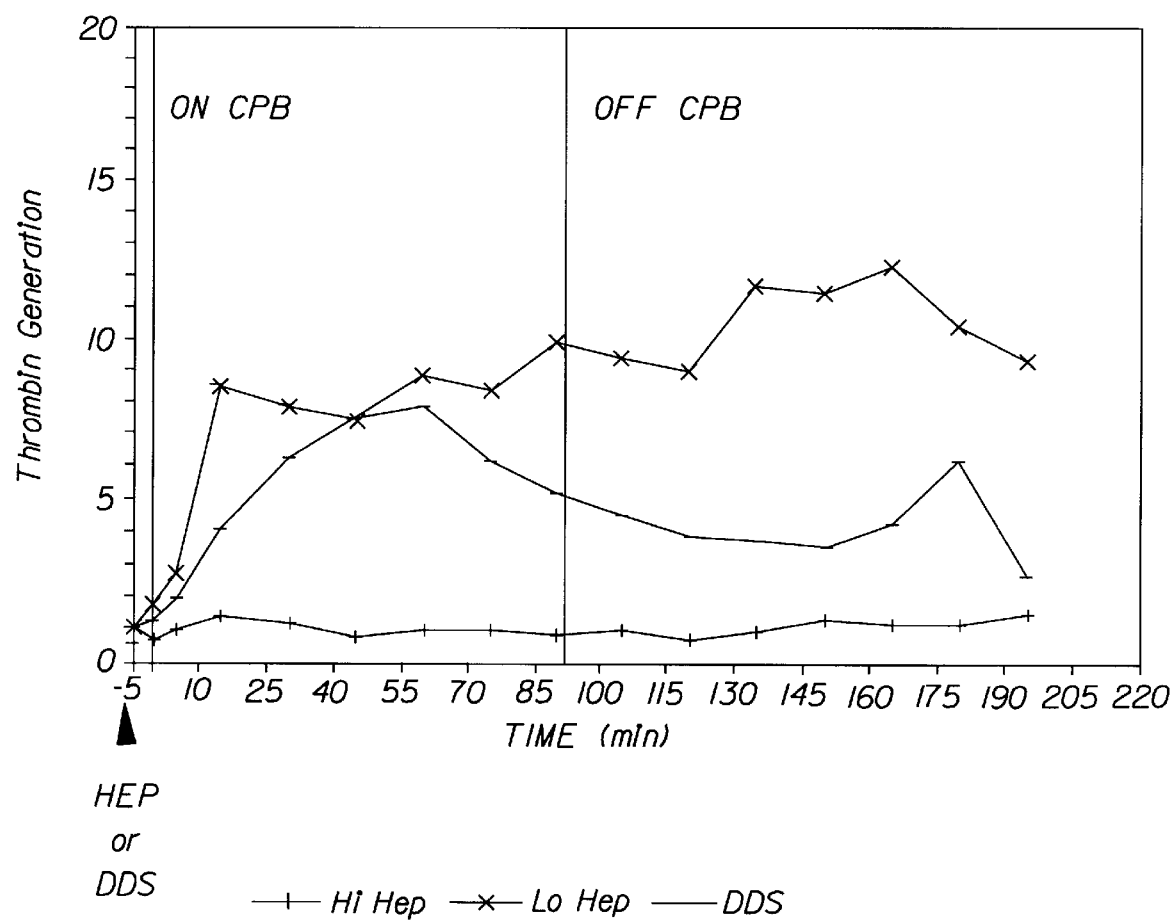
FIG. 7 shows a graphical representation of Anti-thrombin activity (Anti-IIa) versus time during CPB in pigs receiving either heparin or DDS.

In DDS treated animals, the ACT did not exceed 270 seconds during CPB and returned to normal within the 2 hour monitoring period (FIG. 4) in DDS treated animals. This ACT was associated with minimal circulating anti-thrombin activity (FIG. 6). TAT levels and T/HCII levels did not increase during the time on CPB (FIG. 7). In HEP 25 treated animals, the findings were similar. The ACT did not exceed 260 seconds during CPB (FIG. 4) and again was associated with minimal circulating anti-thrombin activity (FIG. 6). In HEP 400 (standard human clinical dose) treated animals the ACT was elevated markedly over baseline as seen in the clinical situation. This was associated with significant anti-thrombin activity (FIG. 6). TAT and T/HCII levels increased during CPB, but were less in either DDS 25 or HEP 25 treated animals (FIG. 7).

These data suggest that 1) DDS/HCII inhibits thrombin more effectively than heparin/ATIII since successful CPB was achieved with DDS at a lower systemic anticoagulant dose, and thrombin generation post CPB was ameliorated with DDS whereas it was not with heparin; and 2) this effect can be achieved with a lower anticoagulant dose, thereby reducing the risk of bleeding.

Example 5

This Example shows how to form other salt forms of DDS.

As is known to those skilled in the art, the salt form determines the affinity for certain ionized electrolytes in blood which may be critical in determining blood gas constituents. The sodium salt of the DDS composition of Example 1 is reacted with the chloride of a different cation to produce other salt forms or blends of different salts. Such ion exchange of the DDS composition may be accomplished by passing over a previously-charged cation exchange resin, slurrying with a chloride solution followed by solvent precipitation or diafiltration against an aqueous solution containing a different chloride.

Alternatively, the DDS composition of the present invention which generally is in a sodium form as a result of neutralization with dilute caustic soda during manufacture, is diluted with purified water to a concentration between about 1 and 15%, preferably about 7%, and subjected to diafiltration through a membrane having a molecular weight cut-off of 1000 Daltons (PCAC of Millipore Corporation, Bedford Mass.) in a suitable apparatus (Pellican, Millipore Corporation, Bedford, Mass.). The concentration of DDS is kept constant by continuous addition of about 0.5–2.0M calcium chloride (adjusted to pH 7.4 with calcium hydroxide). Any excess of calcium chloride is removed by diafiltration by continuous addition of purified water and the calcium salt of DDS recovered by lyophilization. A typical yield of the transformation is greater than 90% having a percent calcium of more than 9.5% and a sodium content of less than 1000 ppm, as determined by flame photometry.

The same approach is used in the production of other salts, including the ammonium, barium, copper, lithium, potassium and zinc salts Example 6

This Example shows the preparation of a fragment of Dermatan Sulfate (DS).

Oxidative-Reductive Depolymerization of Dermatan Sulfate—50 grams of native DS (Celsus Laboratories, Cincinnati, Ohio Lot No. DI-10394) having an average molecular weight of 35000 Daltons, sulfur and nitrogen contents of 2.0 and 6.59%, respectively, and a heparin assay of 4 u/mg, was diluted with purified water to a concentration of 10% (w/v). Under agitation, Duolite C-20 (Rohm & Hass, Philadelphia, Pa.), previously regenerated with hydrochloric acid, was added to reduce the pH to 2.5, at which point the resin was removed by filtration through a Buchner funnel. With agitation the DS solution was then preheated to 75° C. and 10 ml of 35% hydrogen peroxide was added, followed by sterilization at 23 psi pressure for 15 minutes. Upon completion of the cycle, the solution was removed from the sterilizer, cooled to less than 40° C. and the pH adjusted to 6.5–7.0 with caustic soda. One volume of ethanol was added to precipitate DS. The precipitate was removed by drying it in vacuo. The depolymerized DS, had the following properties:

TABLE 4

Typical Properties of a Fragment of DS

| Recovery, g | 40 |
|---|---|
| Average Molecular Weight | 5,600 |
| Assay, u/mg | <2 |
| Nitrogen, % | 2.42 |
| Total Sulfur, % | 6.49 |

Example 7

This Example shows a method for the preparation of a fragment of Dermatan Disulfate (DDS).

DDS may be esterified at its uronic acid carboxyl groups and cleaved by controlled β-elimination under alkaline conditions employing procedures known to one skilled in the art. In this process, DDS is converted to an organic solvent-soluble form by contact with a hydrophobic quaternary ammonium salt such as Hyamine 1622. To a solution of the Hyamine salt of DDS in a solvent such as dimethylformamide, benzyl (or a suitably substituted benzyl) chloride is added and the substances are left in contact for 3 days at ambient temperature. Then, an equal volume of a 10% solution of sodium acetate in methanol is added and the precipitate formed is separated by filtration, washed with methanol and dried in vacuo to yield the sodium salt of the DDS ester. The product is characterized by the ultraviolet absorption of the benzyl group around 200 nm. The benzyl ester is then subjected to alkaline β-elimination under conditions well known to those skilled in the art.

Alternatively, DDS is dissolved in 0.15M acetate-0.15M NaCl-0.005M CaCl-pH 6.9. After addition of polysaccharide lyase, the mixture is incubated at ambient temperature until the average molecular mass of the disulfate is reduced to about 5000 Daltons. The depolymerization is monitored by the increase in ultraviolet absorption at 232 nm (due to the production of a double bond at the non reducing end of the saccharide) and by measuring the average molecular mass of the polymer mixture by viscometry.

Example 8

This Example shows the preparation of fractions of Dermatan Sulfate (DS) and Dermatan Disulfate (DDS).

Native dermatan sulfate (DS) may be fractionated followed by sulfation. Fractionation techniques known to those skilled in the art to be applicable to DS and other structurally-related glycosaminoglycans (Linhardt, R. J., Desai, U. R., Liu, J., Pervin A., Hoppensteadt D., Fareed J., Low Molecular Weight Dermatan Sulfate As An Antithrombotic Agent, Biochem Pharmacol 49: 1241–1252 (1994)) include solvent fractionation, ultrafiltration, and ion exchange, affinity and gel chromatography.

Charge Density Fractionation of DS—A 7.5"×50" column containing anion exchange resin (Lewatit S-6238-A, Bayer, Pittsburgh Pa.) was regenerated with hydrochloric acid, thoroughly rinsed with Purified Water USP and equilibrated with 29 liters of 0.5 molar NaCl. Then, 400 grams of DS, lot #DI-10094, dissolved in 19 liters of 0.5 molar NaCl was charged to the column at a flow rate of 200 ml/min. The column was then washed with an additional 12 liters of 0.5 molar NaCl. Subsequently, 28 liters of DF-104-1 was collected at 200 ml/min, diafiltered against Purified Water USP to a conductivity of less than 200 $\mu$S, identified for carbohydrates by a qualitive Molisch test (Dische Z. General color reactions. Mtds Carbohydr Chem 1963;I: 478–81), concentrated by ultrafiltration and freeze dried. Other subfractions were eluted in a similar manner by charging to the column 28 liter increments of 1.2, 1.6 and 2.0 molal NaCl for the collection of fractions DF-104-2 through DF-104-4. See Table 5.

TABLE 5

Fractions of Native Dermatan Sulfate Obtained by Charge Density Fractionation

|  | DS-10494 | DF-104-1 | DF-104-2 | DF-104-3 | DF-104-4 |
|---|---|---|---|---|---|
| Recovery, g |  | 164 | 64 | 118 | 40 |
| Molecular Weight | 36,000 | 51,366 | 26,801 | 26,653 | 23,116 |
| Optical Rotation, ° | −62 |  |  |  | −31 |
| Assay, u/mg | 5 | <2 | <2 | 10 | >15 |
| Nitrogen, % | 2.33 | 2.60 | 2.57 | 2.68 | 2.22 |
| Total Sulfur, % | 7.16 | 6.27 | 5.99 | 6.83 | 6.61 |
| Anti-IIa, U/mg | 7 | 6 | 2 | 6 | 10 |
| Anti-Xa, U/mg | 9 | 1 | 2 | 12 | >15 |

Charge Density Fractionation of DDS—5 gram of OD-00195 was dissolved in 750 ml of 0.5 molar NaCl and applied to a 4.4×43 cm column equilibrated with 0.5 molar NaCl at a flow rate of 100 ml/h. The column was washed with one column volume of 0.5 molar NaCl. The breakthrough combined with the 1.4 and 1.6 molar eluates was collected as 001951. A 2 molar NaCl eluate was collected as 001952. After stopping the column, a second 2 molar eluate was collected as 001953. The main eluate with 2.5 molar NaCl was collected as 001954. After stopping the column overnight, a second 2.5 molar NaCl eluate was collected as 001955. After stopping overnight, the column was then washed. Elution with 3 molar NaCl failed to elute additional material. The data shown in Table 6 suggest that charge density is an effective method of optimizing Anti-IIa activity of DDS.

TABLE 6

Fractions of DDS obtained by Charge Density Fractionation

|  | 001951 | 001952 | 001953 | 001954 | 001955 |
|---|---|---|---|---|---|
| Recovery, g | 0.08 | 0.4 | 0.2 | 3.8 | 0.5 |
| Ave Mol Wt | 14,434 | 16,613 | 37,305 | 30,169 | 31,654 |
| Anti-IIa, u/mg | <18 | 30 | 71 | 74 | 64 |

Example 9

This Example shows the preparation of a Dermatan Disulfate-based thromboresistant coating.

DDS in water is mixed with a stoichiometric excess of an aqueous solution of a hydrophobic quaternary ammonium salt such as benzalkonium chloride, tridodecylmethylammonium chloride or other salt known to one skilled in the art. The resulting quaternary ammonium salt of DDS is collected by vacuum filtration, washed extensively with water, and dried in vaco. This salt, insolube in water or dilute saline solution, is dissolved in ethanol, isopropanol or other appropriate organic solvent and used to coat artificial surfaces which may come in contact with the bloodstream.

Example 10

This Example shows the Covalently-Immobilized Dermatan Disulfate.

Copolymers of amines and DDS may be irreversibly attached to polymers by gamma irradiation, a technique known in the art as radiation grafting.

Alternatively, DDS is allowed to react in aqueous solution at pH3 and 4° C. with a stoichiometrically limiting amount of sodium metaperiodate for 24 hours. During this time a small portion of the unsulfated uronic acid residues in DDS are cleaved with periodate and the newly formed aldehyde groups are detected and quantified by the MBTH assay (Sawicki, E., T. R., Stanely, T. W. and Elbert, W. Anal. Chem. 33, 93–96 1961). The cleaved DDS derivative is recovered by precipitation with 3 volumes of 95% ethanol, decantation, and dissolution in 1M sodium chloride. The derivative is then purified by reprecipitation with 3 volumes of 95% ethanol, collected by decantation or filtration, dehydrated sequentially with 95% ehtanol and acetone by trituration with the solvent and collection of the solid by decantation or filtration. Trapped solvents are removed in vacuo to yield a white solid. The activated DDS derivative may now be covalently immobilized on amine-bearing materials by Schiff base formation and reduction with sodium cyanoborohydride utilizing conditions well known to those skilled in the art.

Although this invention has been primarily described in terms of specific examples and embodiments thereof, it is evident that the foregoing description will suggest many alternatives, modifications, and variations to those of ordinary skill in the art. Accordingly, the appended claims are intended to embrace as being within the spirit and scope of invention, all such alternatives, modifications, and variations.

We claim:

1. A composition comprising dernatan sulfate having more than about 75% repeating L-iduronic acid->4,6-di-O-sulfated N-acetyl-D-galactosarnine disaccharide units.

2. The composition of claim 1 wherein the dermatan sulfate has a cationic counterion, and wherein said cationic counterion is sodium.

3. The composition of claim 1 wherein the dermatan sulfate has a cationic counterion selected from the group consisting of ammonium, barium, calcium, copper, iron, lithium, potassium and zinc.

4. The composition of claim 2 which is prepared by chemical sulfation of native dermatan sulfate.

5. The composition of claim 1 which is prepared by complete chemical synthesis.

6. The composition of claim 4 wherein the native dermatan sulfate is isolated from natural sources that are then purified.

7. The composition of claim 1 which is purified by charge density fractionation of a heterogeneous preparation of dermatan sulfate.

8. A method of inhibiting thrombin generation comprising: administering to patient in need of a treatment for inhibition of thrombin generation, a composition containing a medicinally effective amount of a dermatan sulfate having more than about 75% repeating L-iduronic acid->4,6-di-O-sulfated N-acetyl-D-galactosamine disaccharide units.

9. The method of claim 8 wherein the average molecular weight of the dermatan sulfate is between about 5,000 and about 30,000 Daltons.

10. The method of claim 8 wherein said composition possesses an anti-IIa activity in the range of between about 25 and about 125 u/mg.

11. The method of claim 8 wherein the cationic counterion of the dermatan sulfate is sodium.

12. The method of claim 8 wherein the dermatan sulfate has a cationic counterion is selected from the group consisting of ammonium, barium, calcium, copper, iron, lithium and potassium.

13. The method of claim 8 wherein the composition is prepared by chemical sulfation of native dermatan sulfate.

14. The method of claim 8 wherein the composition is prepared by complete chemical synthesis.

15. The dermatan sulfate of claim 13 wherein the native dermatan sulfate is isolated from natural sources that are then purified.

16. The method of claim 8 wherein said composition has been purified by charge density fractionation of a heterogeneous preparation of dermatan sulfate.

17. The method of claim 8 wherein the step of administering further includes administering said composition in vivo.

18. The method of claim 8 wherein the step of administering further includes administering said composition parenterally.

19. The method of claim 8 wherein the step of administering further includes administering said composition orally.

20. The method of claim 8 wherein the step of administering further includes administering said composition in vitro.

21. A method of inhibiting complement activation comprising: administering to patient in need of a treatment for inhibiting complement activation, a composition containing a medicinally effective amount of a dermatan sulfate having more than about 75% repeating L-iduronic acid->4,6-di-O-sulfated N-acetyl-D-galactosamine disaccharide units.

22. The method of claim 21 wherein the average molecular weight of the dermatan sulfate is between about 5,000 and about 30,000 Daltons.

23. The method of claim 22 wherein said composition possesses an anti-IIa activity in the range of between about 25 and about 125 u/mg.

24. The method of claim 21 wherein the cationic counterion of the dermatan sulfate is sodium.

25. The method of claim 21 wherein the dermatan sulfate has a cationic counterion selected from the group consisting of ammonium, barium, calcium, copper, iron, lithium and potassium.

26. The method of claim 21 wherein the composition is prepared by chemical sulfation of native dermatan sulfate.

27. The method of claim 21 wherein the composition is prepared by complete chemical synthesis.

28. The dermatan sulfate of claim 26 wherein the native dermatan sulfate is isolated from natural sources that are then purified.

29. The method of claim 21 wherein said composition has been purified by charge density fractionation of a heterogeneous preparation of dermatan sulfate.

30. The method of claim 21 wherein the step of administering further includes administering said composition in vivo.

31. The method of claim 21 wherein the step of administering further includes administering said composition parenterally.

32. The method of claim 21 wherein the step of administering further includes administering said composition orally.

33. The method of claim 21 wherein the step of administering further includes administering said composition in vitro.

34. A method of inhibiting intimal hyperplasia comprising: administering to a patient in need of a treatment for inhibition of intimal hyperplasia a composition containing a medicinally effective amount of a dermatan sulfate having more than about 75% repeating L-iduronic acid->4,6-di-O-sulfated N-acetyl-D-galactosamine disaccharide units.

35. The method of claim 34 wherein the average molecular weight of the dermatan sulfate administered is between about 5,000 and about 30,000 daltons.

36. The method of claim 34 wherein said dermatan sulfate possesses an anti-IIa activity in the range of between about 25 and about 125 u/mg.

37. The method of claim 34 wherein the cationic counterion of the dermatan sulfate is sodium.

38. The method of claim 34 wherein the dermatan sulfate has a cationic counterion selected from the group consisting of ammonium, barium, calcium, copper, iron, lithium, sodium and potassium.

39. The method of claim 34 wherein the composition is prepared by chemical sulfation of native dermatan sulfate.

40. The method of claim 34 wherein the composition is prepared by complete chemical synthesis.

41. The dermatan sulfate of claim 39 wherein the native dermatan sulfate is isolated from natural sources that are then purified.

42. The method of claim 34 wherein said composition has been purified by charge density fractionation of a heterogeneous preparation of dermatan sulfate.

43. The method of claim 34 wherein the step of administering further includes administering said composition iin vivo.

44. The method of claim 34 wherein the step of administering further includes administering said composition parenterally.

45. The method of claim 34 wherein the step of administering further includes administering said composition orally.

46. The method of claim 34 wherein the step of administering further includes administering said composition in vitro.

* * * * *